(12) United States Patent
Argentine

(10) Patent No.: US 10,406,012 B2
(45) Date of Patent: Sep. 10, 2019

(54) MECHANICAL DELIVERY SYSTEMS FOR AN ENDOVASCULAR DEVICE

(71) Applicant: Medtronic Vascular, Inc., Santa Rosa, CA (US)

(72) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 113 days.

(21) Appl. No.: 15/498,198

(22) Filed: Apr. 26, 2017

(65) Prior Publication Data

US 2018/0311060 A1 Nov. 1, 2018

(51) Int. Cl.
  *A61F 2/966* (2013.01)
  *A61F 2/07* (2013.01)
  *A61F 2/95* (2013.01)

(52) U.S. Cl.
  CPC ...... *A61F 2/966* (2013.01); *A61F 2002/9517* (2013.01)

(58) Field of Classification Search
  CPC .......... A61F 2002/9517; A61F 2/95–97; A61F 2002/9505–9665; A61F 2/01–013; A61F 2002/011–018; A61F 2/2427–2/2439
  See application file for complete search history.

(56) References Cited

U.S. PATENT DOCUMENTS

| | | | |
|---|---|---|---|
| 9,445,928 B2* | 9/2016 | Argentine | ............... A61F 2/966 |
| 9,486,350 B2 | 11/2016 | Argentine | |
| 10,258,468 B2* | 4/2019 | Deem | ...................... A61F 2/243 |
| 2003/0028236 A1* | 2/2003 | Gillick | ...................... A61F 2/95 |
| | | | 623/1.11 |
| 2005/0080476 A1* | 4/2005 | Gunderson | ............... A61F 2/95 |
| | | | 623/1.11 |
| 2005/0149159 A1 | 7/2005 | Andreas et al. | |
| 2005/0273151 A1* | 12/2005 | Fulkerson | ............... A61F 2/966 |
| | | | 623/1.11 |

(Continued)

FOREIGN PATENT DOCUMENTS

WO   2007/022395 A1   2/2007

OTHER PUBLICATIONS

International Search Report and Written Opinion dated Jun. 21, 2018 in corresponding European Patent Application No. PCT/US2018/026857.

*Primary Examiner* — Shaun L David
*Assistant Examiner* — Brigid K Byrd

(57) ABSTRACT

A delivery system for delivering a prosthesis includes a housing, a sheath extending from within the housing, a first rotatable knob, a first pulley coupled to the first rotatable knob so as to be rotatable therewith, a second rotatable knob, a second pulley coupled to the second rotatable knob so as to be rotatable therewith, and a cable coupled to the first pulley and to the second pulley. The cable is coupled to a proximal portion of the sheath. Rotation of the first rotatable knob causes the first pulley to rotate while the second pulley remains stationary thereby causing the first pulley to wind up a portion of the cable and retract the sheath at a first speed. Rotation of the second rotatable knob causes both the first and second pulleys to rotate, thereby causing both the first and second pulleys to wind up a portion of the cable and retract the sheath at a second speed being faster than the first speed.

20 Claims, 14 Drawing Sheets

(56) References Cited

U.S. PATENT DOCUMENTS

| | | | |
|---|---|---|---|
| 2006/0136034 A1* | 6/2006 | Modesitt | A61F 2/88 623/1.11 |
| 2007/0060999 A1* | 3/2007 | Randall | A61F 2/95 623/1.11 |
| 2007/0112355 A1* | 5/2007 | Salahieh | A61F 2/2418 606/108 |
| 2007/0123971 A1* | 5/2007 | Kennedy, II | A61F 2/95 623/1.11 |
| 2007/0168014 A1* | 7/2007 | Jimenez | A61F 2/95 623/1.12 |
| 2007/0191865 A1* | 8/2007 | Pappas | A61F 2/966 606/108 |
| 2007/0219617 A1* | 9/2007 | Saint | A61F 2/95 623/1.12 |
| 2007/0293934 A1* | 12/2007 | Grewe | A61F 2/95 623/1.12 |
| 2008/0188920 A1* | 8/2008 | Moberg | A61F 2/95 623/1.12 |
| 2009/0018553 A1 | 1/2009 | McLean et al. | |
| 2009/0024133 A1* | 1/2009 | Keady | A61F 2/95 606/99 |
| 2009/0099638 A1* | 4/2009 | Grewe | A61F 2/966 623/1.11 |
| 2009/0210046 A1* | 8/2009 | Shumer | A61F 2/95 623/1.11 |
| 2010/0036472 A1* | 2/2010 | Papp | A61F 2/95 623/1.11 |
| 2010/0168756 A1* | 7/2010 | Dorn | A61F 2/95 606/108 |
| 2010/0174290 A1* | 7/2010 | Wuebbeling | A61F 2/95 606/108 |
| 2010/0274227 A1* | 10/2010 | Khairkhahan | A61B 17/12022 604/533 |
| 2011/0282425 A1 | 11/2011 | Dwork | |
| 2011/0288558 A1* | 11/2011 | Nimgaard | A61F 2/95 606/108 |
| 2012/0041537 A1* | 2/2012 | Parker | A61F 2/95 623/1.11 |
| 2012/0053574 A1 | 3/2012 | Murray, III et al. | |
| 2012/0209317 A1 | 8/2012 | Oepen | |
| 2012/0330401 A1* | 12/2012 | Sugimoto | A61F 2/915 623/1.12 |
| 2013/0018451 A1* | 1/2013 | Grabowski | A61F 2/966 623/1.12 |
| 2013/0184805 A1* | 7/2013 | Sawada | A61F 2/97 623/1.11 |
| 2013/0231735 A1* | 9/2013 | Deem | A61F 2/243 623/2.11 |
| 2014/0135909 A1* | 5/2014 | Carr | A61F 2/2436 623/2.11 |
| 2014/0180381 A1* | 6/2014 | Kelly | A61F 2/966 623/1.11 |
| 2014/0257454 A1* | 9/2014 | McGee | A61F 2/966 623/1.11 |
| 2014/0324151 A1* | 10/2014 | Yamashita | A61F 2/82 623/1.11 |
| 2014/0358156 A1* | 12/2014 | Argentine | A61F 2/966 606/108 |
| 2015/0250630 A1* | 9/2015 | Irwin | A61F 2/95 606/108 |
| 2015/0305902 A1* | 10/2015 | Argentine | A61F 2/966 623/1.12 |
| 2016/0074190 A1* | 3/2016 | Cummins | A61F 2/966 623/1.11 |
| 2016/0135975 A1* | 5/2016 | Shimoyama | A61F 2/844 623/1.12 |
| 2018/0133007 A1* | 5/2018 | Prabhu | A61B 90/06 |
| 2018/0250150 A1* | 9/2018 | Majercak | A61B 17/3468 |

* cited by examiner

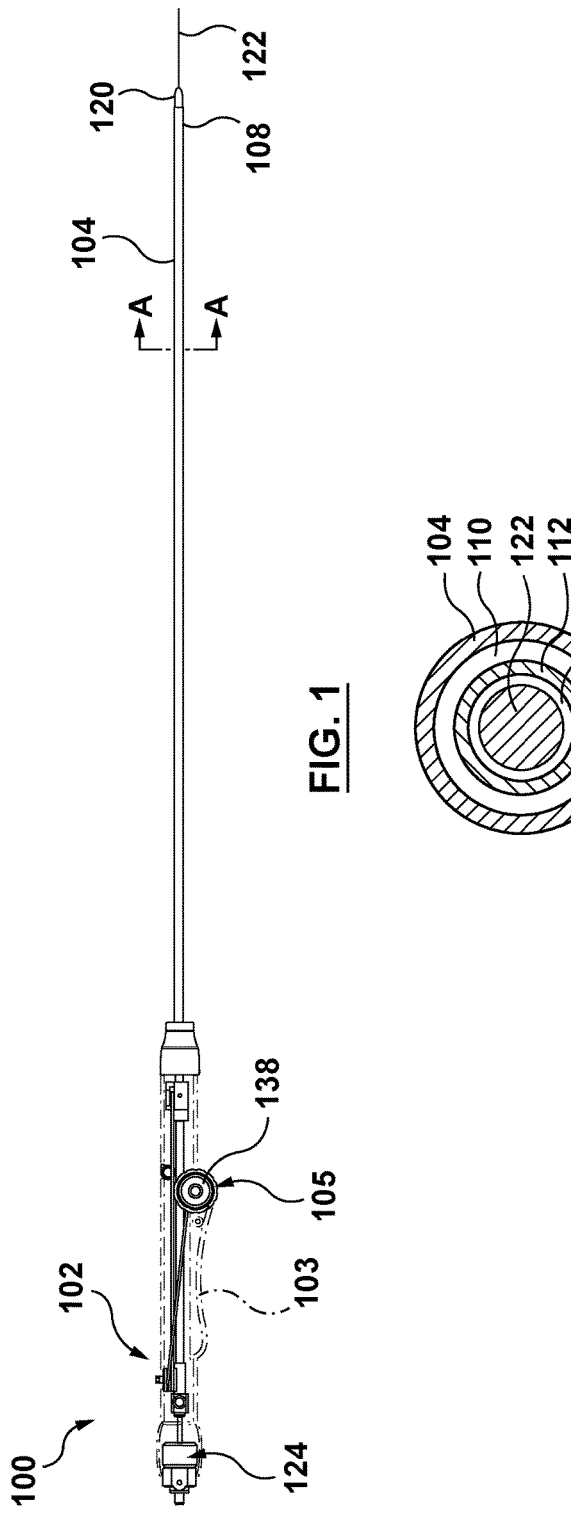
FIG. 1
FIG. 1A
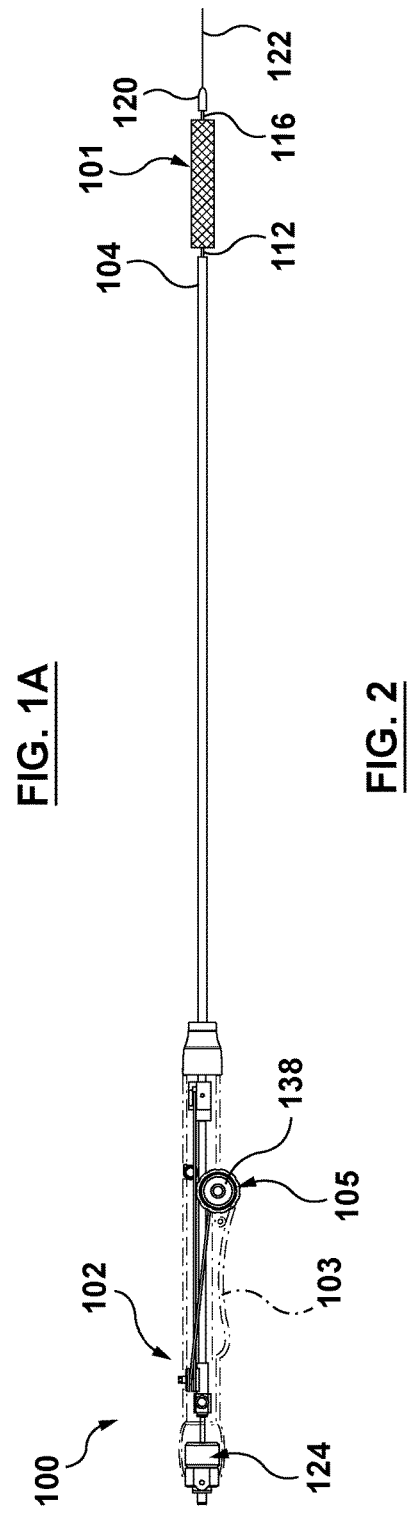
FIG. 2

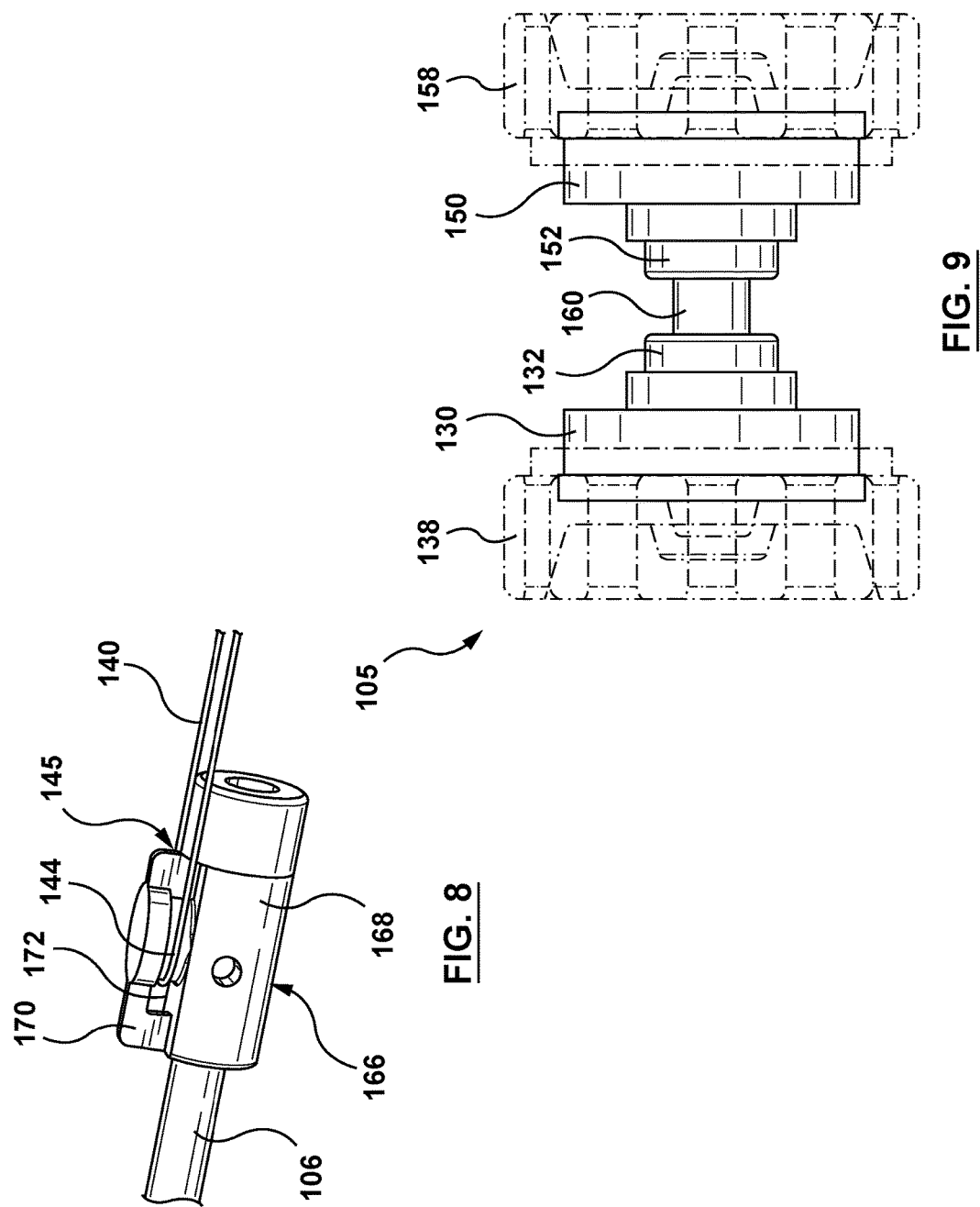

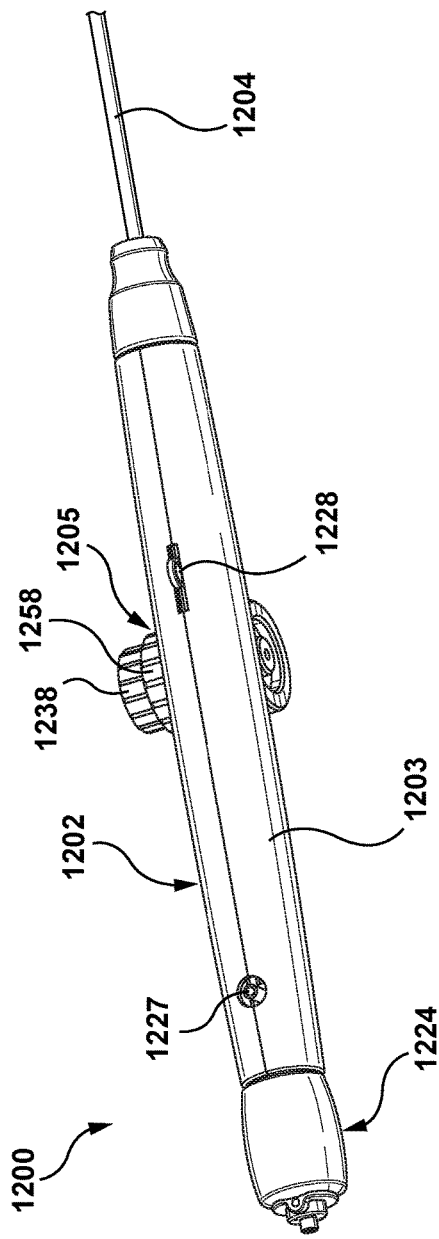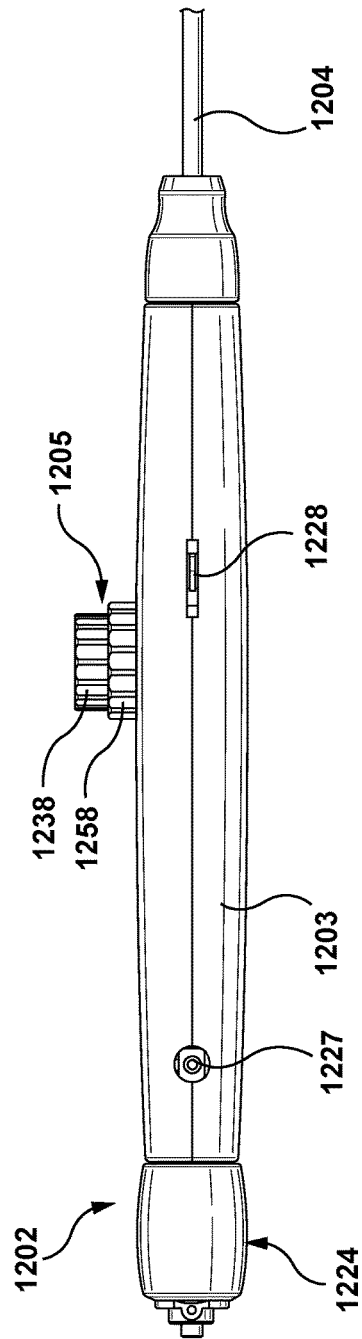
FIG. 12
FIG. 13

MECHANICAL DELIVERY SYSTEMS FOR AN ENDOVASCULAR DEVICE

FIELD OF THE INVENTION

The invention is related in general to implantable prostheses and in particular to self-expanding stent-grafts.

BACKGROUND OF THE INVENTION

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expandable stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes arranged for relative axial movement. For example, a self-expanding stent-graft may be compressed and disposed within the distal end of an outer catheter tube distal of a stop fixed to the inner member. The catheter is then maneuvered, typically routed through a body lumen until the end of the catheter and the stent-graft are positioned at the intended treatment site. The stop on the inner member is then held stationary while the outer tube of the delivery catheter is withdrawn. The stop prevents the stent-graft from being withdrawn with the sheath. As the sheath is withdrawn, the stent-graft is released from the confines of the sheath and radially self-expands so that at least a portion of it contacts and substantially conforms to a portion of the surrounding interior of the lumen, e.g., the blood vessel wall or anatomical conduit.

In recent years, to improve optimal control and alignment during deployment and positioning of a stent-graft, various tip capture spindles have been incorporated into the delivery system utilized for percutaneously delivering the stent-graft prosthesis. Tip capture involves restraining the proximal end stent of the stent-graft in a radially compressed configuration in conjunction with the main body restraint achieved by other delivery system components, such as a tubular cover shaft or sheath. The tip capture spindle can be activated at any time during stent-graft deployment to suit any number of system characteristics driven by the therapy type, stent-graft type, or specific anatomical conditions that may prescribe the release timing. Typically, the tip capture release is activated after some or all the main stent-graft body release, and thus provides a mean of restraining the stent-graft during positioning and any re-positioning. Additional restraint of the stent-graft is a key characteristic when the operator is attempting to accurately position the stent relative to an anatomical target. The tip capture restraint also aids in reducing an abrupt force of expansion when the stent-graft is released from the graft cover or sheath.

A stent-graft may be tightly compressed within a catheter for delivery, imposing high levels of friction between the stent-graft and the outer sheath of the catheter. Thus, a delivery system must be capable of imparting a significant, yet controlled, force to retract the outer sheath and deploy the stent-graft. A need in the art still exists for an improved delivery system having a handle that consistently and reliably retracts the outer sheath thereof in order to deploy a prosthesis in a body lumen.

BRIEF SUMMARY OF THE INVENTION

Embodiments hereof relate to a delivery system for delivering a prosthesis. The delivery system includes a housing, a sheath extending from within the housing, a first rotatable knob accessible from an exterior of the housing, a first pulley coupled to the first rotatable knob so as to be rotatable therewith, a second rotatable knob accessible from an exterior of the housing, a second pulley coupled to the second rotatable knob so as to be rotatable therewith, and at least one cable coupled to the first pulley and to the second pulley. The at least one cable is coupled to a proximal portion of the sheath. Rotation of the first rotatable knob causes the first pulley to rotate while the second pulley remains stationary thereby causing the first pulley to wind up a portion of the at least one cable and retract the sheath at a first speed. Rotation of the second rotatable knob causes both the first and second pulleys to rotate, thereby causing both the first and second pulleys to wind up a portion of the at least one cable and retract the sheath at a second speed, the second speed being faster than the first speed.

Embodiments hereof also relate to a delivery system that includes a housing, a sheath extending from within the housing, a first rotatable knob accessible from an exterior of the housing, a first pulley coupled to the first rotatable knob so as to be rotatable therewith, a second rotatable knob accessible from an exterior of the housing, a second pulley coupled to the second rotatable knob so as to be rotatable therewith, and at least one cable coupled to the first pulley and to the second pulley. The at least one cable is coupled to a proximal portion of the sheath. The first pulley is configured to be rotated independently with rotation of the first rotatable knob and the first and second pulleys are configured to be rotated simultaneously with rotation of the second rotatable knob. Rotation of the first rotatable knob causes the first pulley to wind up a portion of the at least one cable and retract the sheath at a first speed. Rotation of the second rotatable knob causes both the first and second pulleys to wind up a portion of the at least one cable and retract the sheath at a second speed, the second speed being faster than the first speed.

Embodiments hereof also relate to a delivery system that includes a housing, a sheath extending from within the housing, a first rotatable knob accessible from an exterior of the housing, a first pulley coupled to the first rotatable knob so as to be rotatable therewith, a second rotatable knob accessible from an exterior of the housing, a second pulley coupled to the second rotatable knob so as to be rotatable therewith, a joining shaft, a first one-way clutch disposed over the joining shaft and attached to the first pulley, a second one-way clutch disposed over the joining shaft and attached to the second pulley, and a single continuous cable having a first end coupled to a first pulley and a second end coupled to a second pulley. The single continuous cable is coupled to a proximal portion of the sheath. Rotation of the first rotatable knob causes the first pulley to rotate and the first one-way clutch freely spins within or over the joining shaft thereby causing the first pulley to wind up a portion of the at least one cable and retract the sheath at a first speed. Rotation of the second rotatable knob causes both the first and second pulleys to rotate via the second one-way clutch transmitting a torque from the second pulley to the joining shaft, thereby causing both the first and second pulleys to wind up a portion of the at least one cable and retract the sheath at a second speed, the second speed being faster than the first speed.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a delivery system according to an embodiment hereof, wherein an outer sheath of the delivery system surrounds and constrains a prosthesis in a compressed or delivery configuration.

FIG. 1A is a cross-sectional view taken along line A-A of FIG. 1.

FIG. 2 is a side view of the delivery system of FIG. 1, wherein the outer sheath has been retracted via a handle of the delivery system in order to allow the prosthesis to self-expand to a deployed or expanded configuration.

FIG. 8 is an enlarged perspective view of a portion of FIG. 6, wherein the single continuous cable is shown looped through an anchor.

FIG. 9 is a side view of components of a sheath retraction mechanism of the handle of the delivery system of FIG. 1, wherein the other components of the handle have been removed for illustrative purposes.

FIG. 12 is a perspective view of a handle of a delivery system according to another embodiment hereof, wherein first and second knobs of the handle are disposed on the same said of the handle.

FIG. 13 is a top view of the handle of FIG. 12.

DETAILED DESCRIPTION OF THE INVENTION

Figure 3:
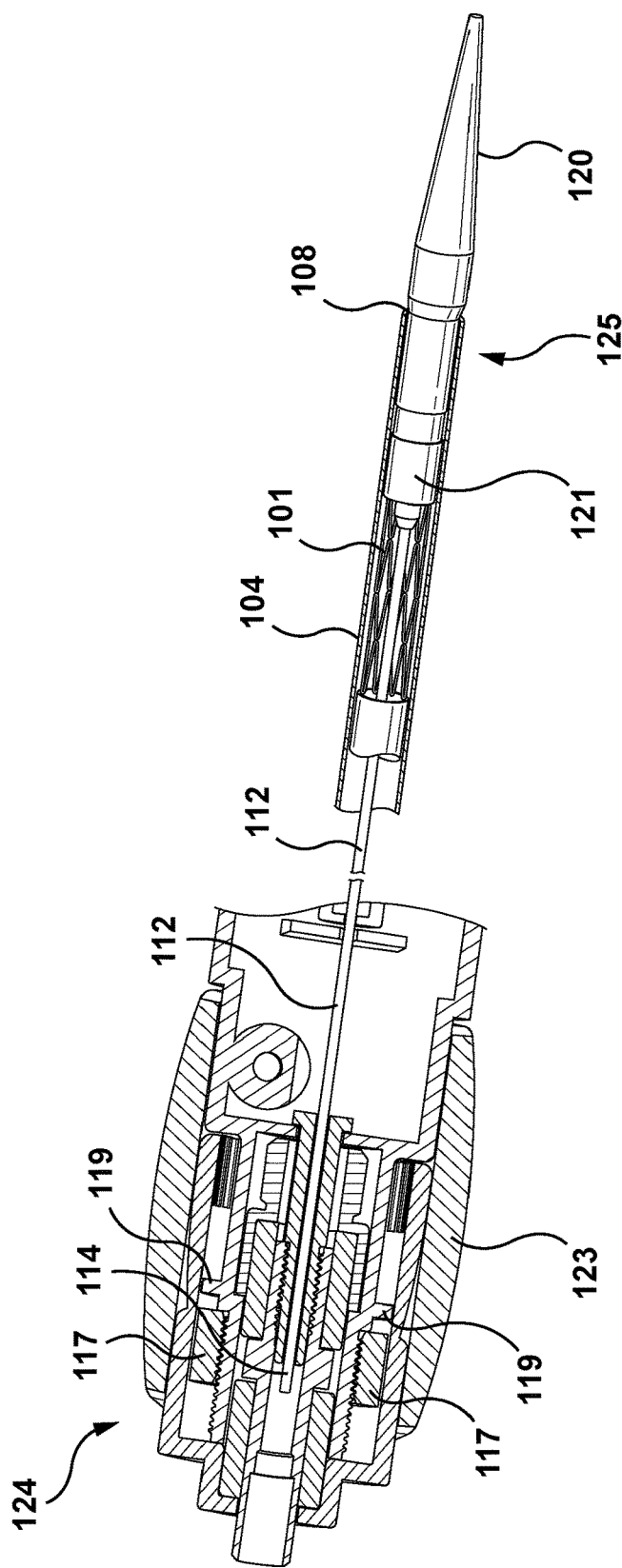
FIG. 3 depicts a sectional view of a tip release mechanism of the handle of the delivery system of FIG. 1 and a tip capture device of the delivery system of FIG. 1.

Specific embodiments of the present invention are now described with reference to the figures, wherein like reference numbers indicate identical or functionally similar elements. Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft prosthesis "proximal" is the portion nearer the heart by way of blood flow path while "distal" is the portion of the stent-graft further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as the aorta, coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments hereof are related to a delivery system having an improved handle that maintains accuracy in delivery and deployment of a prosthesis in a body lumen. With reference to FIGS. 1, 1A, and 2, a delivery system 100 includes a handle 102 having a housing 103, an inner shaft 112 having a proximal end 114 (shown on FIG. 3) and a distal end 116, and an outer retractable sheath or cover 104 having a proximal end 106 (shown on FIGS. 7 and 8) and a distal end 108. Both outer sheath 104 and inner shaft 112 extend from within housing 103 of handle 102. FIG. 1 is a side view of delivery system 100, with outer sheath 104 shown in a delivery configuration in which outer sheath 104 surrounds and constrains a prosthesis 101 in a compressed or delivery configuration. FIG. 1A is a cross-sectional view taken along line A-A of FIG. 1. FIG. 2 is a side view of delivery system 100 after outer sheath 104 has been retracted via handle 102 in order to allow prosthesis 101 to self-expand to a deployed or expanded configuration. Handle 102 includes a tip capture mechanism 124, which will be explained in more detail herein with respect to FIG. 3, and a sheath retraction mechanism 105 for retracting outer sheath 104 as will be explained in more detail herein with respect to FIGS. 4-11. As best shown in FIG. 1A, outer sheath 104 defines a lumen 110 and outer sheath 104 is slidingly disposed over inner shaft 112. Inner shaft 112 defines a lumen 118 such that delivery system 100 may be slidingly disposed and track over a guidewire 122. A tapered flexible nosecone or tip 120 may be coupled to distal end 116 of inner shaft 112. Prosthesis 101 is mounted over inner shaft 112 at a distal portion thereof and outer sheath 104 surrounds and constrains prosthesis 101 in a compressed or delivery configuration as shown in the side view of FIG. 1 (prosthesis 101 shown only in the view of FIG. 2). Proximal end 106 of outer sheath 104 is operably coupled to sheath retraction mechanism 105 of handle 102. During deployment of prosthesis 101, sheath retraction mechanism 105 is operated in order to proximally retract outer sheath 104 to thereby incrementally expose prosthesis 101. Once prosthesis 101 is properly positioned, outer sheath 104 is retracted to fully expose prosthesis 101 and thereby permit full release of prosthesis 101 from delivery system 100, as explained in more detail below. The deployed configuration of prosthesis 101 is merely exemplary, and it would be apparent to one of ordinary skill in the art that delivery system 100 may be utilized for delivering and deploying various types or configurations of self-expanding prostheses.

According to an embodiment hereof, handle 102 also includes a flush shaft or lumen 126 having a port 127 that is accessible from an exterior of housing 103 of handle 102. Flush shaft 126 is concentrically disposed over a proximal portion of inner shaft 112, and the lumen of flush shaft 126 is in fluid communication with lumen 110 of outer sheath 104. Flush shaft 126 may be utilized to flush out or eliminate air in the delivery system and/or prosthesis 101 to prevent such air from being released into the blood stream as will be understood by one of ordinary skill in the art.

FIG. 3 depicts a sectional view of tip release mechanism 124 of handle 102 attached to proximal end 114 of inner shaft 112 and a tip capture device 125 of delivery system 100 that is attached to distal end 116 of inner shaft 112. For ease of illustration a remainder of delivery system 100 is removed from FIG. 3 with a portion of prosthesis 101 being shown in a compressed, delivery configuration within a distal portion of outer sheath 104. Tip capture mechanism 124 is described in more detail in U.S. Pat. No. 9,486,350 to Argentine, which is hereby incorporated by reference herein in its entirety. In a delivery configuration, distal end 108 of outer sheath 104 abuts with tip capture device 125, such that together outer sheath 104 and tip capture device 125 hold a stent-graft in a compressed delivery configuration within a distal portion of delivery system 101. A proximal end of prosthesis 101 is held within a distal sleeve 121 and a spindle (not shown in FIG. 3) of tip capture device 125. Tip release mechanism 124 is operably coupled to tip capture device 125 such that rotation of inner shaft 112 in a first direction moves or distally advances distal sleeve 121 relative to the spindle and a proximal end of prosthesis 101 is released in two distinct steps or stages, wherein during a first step or stage the proximal end of prosthesis 101 is partially uncovered and during a second step or stage the proximal end of prosthesis 101 is fully uncovered and released from tip capture device 125. Tip release mechanism 124 includes a rotatable grip component 123 that is operably coupled to proximal end 114 of inner shaft 112. As more fully described in U.S. Pat. No. 9,486,350 to Argentine, previously incorporated by reference, rotation of grip component 123 in each of a first and second direction rotates the inner shaft 112 in the first direction, which causes distal advancement of distal sleeve 121 of tip capture device 125 to provide the two-stage release of the proximal end of prosthesis 101. Rotation of grip component 123 in the first direction concurrently longitudinally translates a stop component 117 in a distal direction until stop component 117 contacts a hard stop 119 of housing 103 of handle 102. The contact of stop component 117 with hard stop 119 prevents further rotation of the grip component 123 in the first direction, as stop component 117 can no longer move in the distal direction. Thereafter rotation of grip component 123 may continue only in the second direction, which longitudinally translates stop component 117 in a proximal direction while maintaining rotation of inner shaft 112 in the first direction to thereby continue the distal advancement of distal sleeve 121.

In operation, when prosthesis 101 held in a delivery configuration by delivery system 101 is to be deployed, sheath retraction mechanism 105 is operated to retract outer sheath 104 in a proximal direction such that distal end 108 no longer covers or extends over the proximal end of prosthesis 101. Grip component 123 is then rotated in the first direction to perform the first step or stage of tip release described above. The first stage of tip release has been performed when grip component 123 can no longer be rotated in the first direction, wherein distal sleeve 121 of tip capture device 125 will have been distally advanced a sufficient distance to partially uncover the proximal end of prosthesis 101, which permits prosthesis 101 to transition from a delivery state to a partially deployed state. With the proximal end of prosthesis 101 in the partially deployed state, a clinician via fluoroscopy may assure proper positioning at a treatment site of the proximal end of prosthesis 101 before full deployment of prosthesis 101. Accordingly, if the proximal end of prosthesis 101 is found to be not properly positioned at this stage of the procedure, the clinician may "push" or otherwise manipulate the proximal end of prosthesis 101 until proper placement is confirmed. Thereafter sheath retraction mechanism 105 is operated to continue proximal retraction of outer sheath 104 until the remaining length of prosthesis 101 is completely uncovered, and thus allowed to release or deploy from delivery system 101. At this point of operation, prosthesis 101 is no longer covered by outer sheath 104 but the proximal end of prosthesis 101 is still coupled to tip capture device 125. Grip component 123 is then rotated in the second direction to perform the second step or stage of tip release described above. Once distal sleeve 121 of tip capture device 125 is distal of the proximal end of prosthesis 101, the second stage of tip release has been performed, wherein the proximal end of prosthesis 101 release from or move free of tip capture device 125 and the proximal end of prosthesis 101 transitions from the partially deployed state to a fully deployed state. With the release of the proximal end of prosthesis 101 from tip capture device 125, prosthesis 101 is fully deployed.

Figure 4:
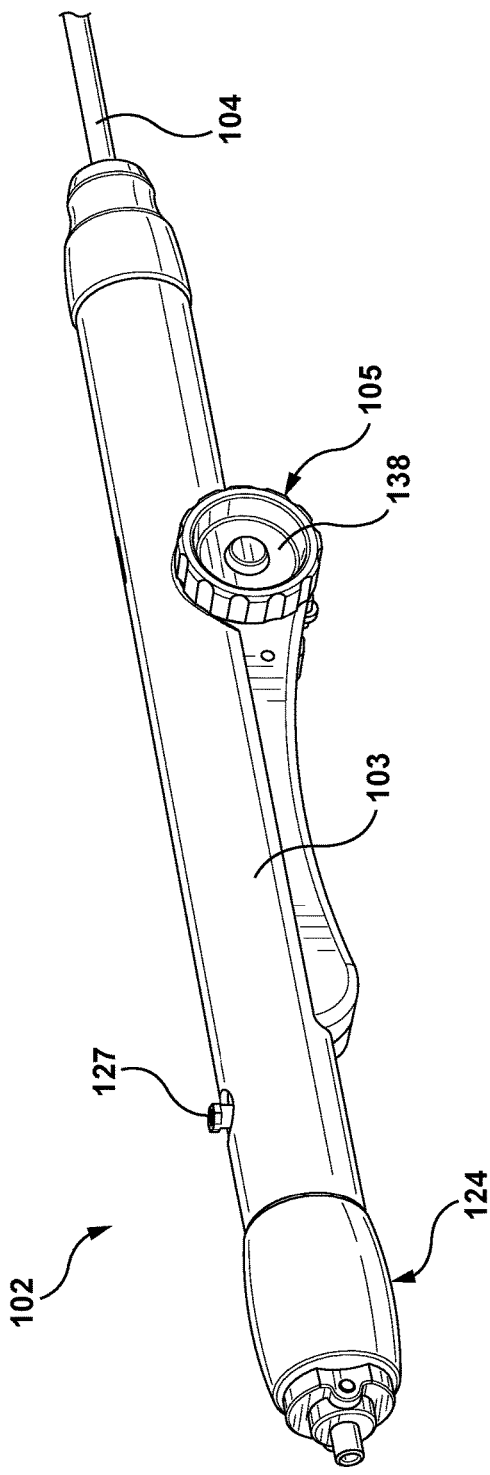
FIG. 4 is a perspective enlarged view of the handle of the delivery system of FIG. 1.
Figure 5:
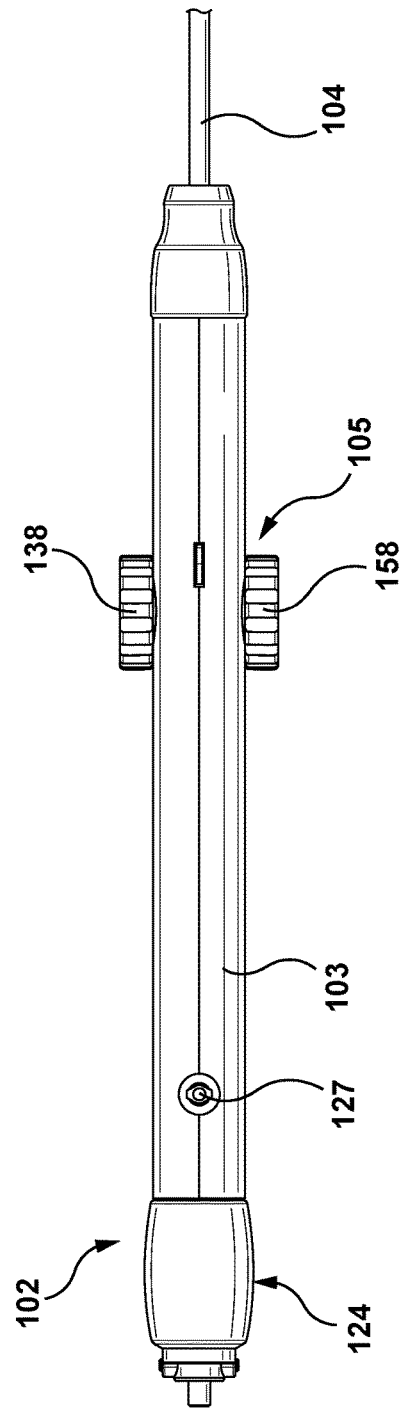
FIG. 5 is a top view of the handle of the delivery system of FIG. 1.
Figure 6:
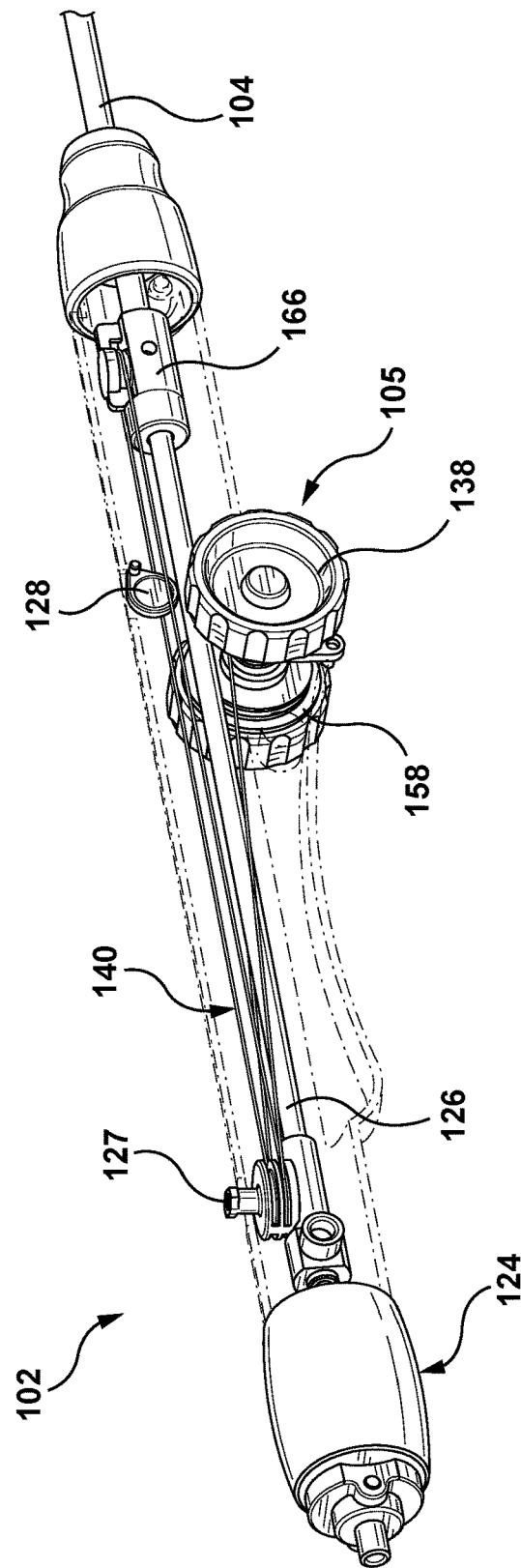
FIG. 6 is a perspective enlarged view of the handle of the delivery system of FIG. 1, wherein a portion of a housing of the handle has been removed for illustrative purposes.

Sheath retraction mechanism 105 for retracting outer sheath 104 will now be described in more detail with respect to FIGS. 4-11. FIGS. 4 and 6 are perspective enlarged views of handle 102, with a portion of housing 103 removed in FIG. 6 to illustrate the internal components of handle 102. FIG. 5 is a top view of handle 102. Sheath retraction mechanism 105 includes a first rotatable knob 138 accessible from an exterior of housing 103 of handle 102, a first pulley 130 coupled to first rotatable knob 138 so as to be rotatable therewith, a second rotatable knob 158 accessible from an exterior of housing 103 of handle 102, a second pulley 150 coupled to second rotatable knob 158 so as to be rotatable therewith, and a single continuous cable 140. In the embodiment of FIGS. 4-11, first and the second rotatable knobs 138, 158 are disposed on opposing sides of handle 102 as best shown on the top view of FIG. 5. Each of first and second pulleys 130, 150 include a circumferential groove or channel formed on an outer surface thereof for receiving single continuous cable 140. First and second rotatable knobs 138, 158 are selectively rotated, turned, spun, or otherwise actuated for proximally retracting outer sheath 104 in order to deploy or release prosthesis 101, thereby allowing prosthesis 101 to self-expand to a deployed or expanded configuration as shown in the side view of FIG. 2. Stated another way, a user operates handle 102 of delivery system 100 in order to withdraw or proximally retract outer sheath 104, thereby releasing prosthesis 101 at a desired location in a patient's body lumen.

As will be explained in more detail herein, rotation of first rotatable knob 138 causes first pulley 130 to rotate while second pulley 150 remains stationary thereby causing first pulley 130 to wind up a portion of cable 140 and retract outer sheath 104 at a first speed. Rotation of second rotatable knob 150 causes both first and second pulleys 130, 150 to rotate, thereby causing both first and second pulleys 130, 150 to wind up a portion of cable 140 and retract outer sheath 104 at a second speed that is faster than the first speed since both pulleys are rotating. Thus, delivery system 100 is configured such that a user may select whether to retract outer sheath 104 with one pulley at a first speed or to retract outer sheath 104 with two pulleys at a second speed, which is faster than the first speed. As such, the user may select to retract outer sheath 104 at a slower rate when desirable, i.e., during the initial stages of retraction when the positioning of prosthesis 101 may still need to be adjusted, and may then select to retract outer sheath 104 at a faster rate when desirable, i.e., during the later stages of retraction when positioning of prosthesis 101 no longer needs to be adjusted. For example, it may be desirable to retract outer sheath 104 at a slower rate prior to tip release via tip capture mechanism 124 and then retract outer sheath 104 at a faster rate after tip release via tip capture mechanism 124. Delivery system 100 includes a rotatable tab or flag 128 which provides a visual indicator for the user when outer sheath 104 has been retracted a predetermined amount. More particularly, when outer sheath 104 has been retracted to rotatable tab or flag 128, an anchor 166 attached to proximal end 106 of outer sheath 104 contacts flag 128 and causes it to rotate or pop up so as to extend out of housing 103 of handle 102. The location of flag 128 is chosen so that it indicates to the user to activate tip capture mechanism 124. For example, flag 128 may pop up after sheath retraction mechanism 105 is operated to retract outer sheath 104 in a proximal direction such that distal end 108 no longer covers or extends over the proximal end of prosthesis 101 as described above with respect to tip capture mechanism 124. The extension or popping up of flag 128 provides a pause during retraction of outer sheath 104 and thereby gives the user a final opportunity to adjust the position of prosthesis 101. As such, a user may retract outer sheath 104 at a slower rate (with only one pulley of delivery system 100) prior to tip release via tip capture mechanism 124, flag 128 indicates timing for tip release, and then the user may retract outer sheath 104 at a faster rate (with both pulleys of delivery system 100) after the first step or stage of tip release has been performed.

Figure 7:
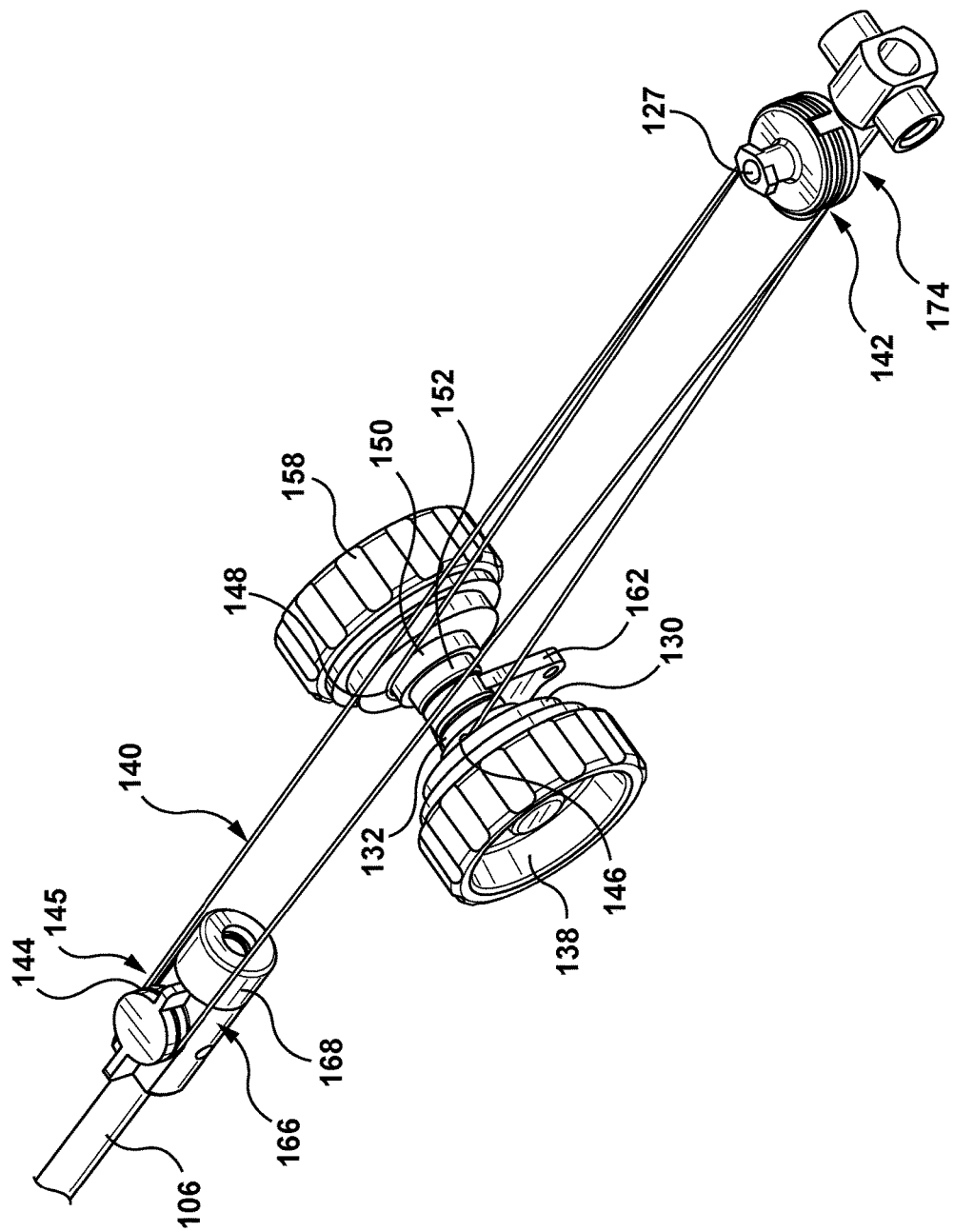
FIG. 7 is a perspective view of select components of the handle of the delivery system of FIG. 1 to illustrate a single continuous cable of the handle of the delivery system of FIG. 1, wherein the other components of the handle have been removed for illustrative purposes.

FIG. 7 is a perspective view of select components of handle 102 to illustrate operation of first and second pulleys 130, 150 with single continuous cable 140. Housing 103 and various other components of the handle have been removed to isolate components described in relation to FIG. 7. In addition to first and second pulleys 130, 150, sheath retraction mechanism 105 further includes single continuous cable 140 having a first end 146 coupled to first pulley 130, a second end 148 coupled to second pulley 150, and an intermediate portion 145 coupled to proximal end 106 of outer sheath 104. Single continuous cable 140 may be formed from any sufficiently strong suitable material, including but not limited to Kevlar® or other suitable synthetic fiber.

As best shown in FIG. 8, intermediate portion 145 of single continuous cable 140 is coupled to proximal end 106 of outer sheath 104 via anchor 166. Anchor 166 includes an annular portion 168 which surrounds and attaches to or is mounted over proximal end 106 of outer sheath 104. Anchor 166 further includes a stem or tab 170 that extends from annular portion 168 and includes a channel or passageway 172 formed therethrough. Intermediate portion 145 of single continuous cable 140 includes a distal loop 144 that extends through passageway 172 of anchor 166 in order to couple the intermediate portion of the single continuous cable to proximal end 106 of outer sheath 104. An advantage of utilizing single continuous cable 140 with first and second pulleys 130, 150 rather than two pulleys that each have a separate cable attached thereto for retracting outer sheath 104 is that single continuous cable 140 is balanced between first and second pulleys 130, 150. As such, each pulley can contribute an equal amount of force to retract outer sheath 104. Conversely, in a system having two pulleys that each have a separate cable attached thereto for retracting outer sheath 104, the two separate cords have a tendency to become unbalanced and one of the pulleys contributes most of or all the force required to retract outer sheath 104. In addition, utilizing a single continuous cable that winds around both first and second pulleys 130, 150 via at least one integral loop (i.e., distal loop 144) rather than two separate cables (i.e., a separate cable for each pulley) provides a mechanical advantage that amplifies the force applied for retracting outer sheath 104. More particularly, when only one of first and second first and second pulleys 130, 150 are rotating, the force output by a single continuous cable that winds around both first and second pulleys 130, 150 may be twice as much as a force output by a system that uses two separate cables. Stated another way, single continuous cable 140 having at least one integral loop (i.e., distal loop 144) provides twice the force for retracting outer sheath 104 at half the speed. The mechanical advantage of first and second pulleys 130, 150 thus minimizes the number of knob rotations or cycles required to fully retract outer sheath 104.

Notably, referring back to FIG. 7, single continuous cable 140 also includes a second intermediate portion having a proximal loop 142 that extends around a portion of a mount 174 that includes port 127 for flush lumen 126. Proximal loop 142 extends around an outer surface of mount 174. As such, single continuous cable 140 is an elongated element with first end 146 coupled to first pulley 130, second end 148 coupled to second pulley 150, and the length of single continuous cable 140 is looped around anchor 166 and mount 174. Having both proximal loop 142 and distal loop 144 further increases the mechanical advantage provided by single continuous cable 140 described above with respect to distal loop 144. However, proximal loop 142 is not required and sheath retraction mechanism 105 provides a mechanical advantage with only one integral loop (i.e., distal loop 144).

The components and operation of sheath retraction mechanism will now be described in more detail with reference to FIGS. 9-11A. FIG. 9 is a side view of select components of sheath retraction mechanism 105. In particular, FIG. 9 illustrates a joining shaft 160, a first one-way clutch 132 disposed over joining shaft 160 and attached to first pulley 138, and a second one-way clutch 152 disposed over joining shaft 160 and attached to second pulley 158. First and second one-way clutches 132, 152 will first be described in more detail with respect to FIGS. 10-10A and FIGS. 11-11A, respectively, prior to a description of the operation of sheath retraction mechanism 105. Joining shaft 160 is mounted within housing 103 of handle 102 via a mount 162 (which is best shown in FIG. 7). Joining shaft 160 is mounted so as to be rotatable within mount 162 and relative to housing 103 of handle 102.

Figure 10A:
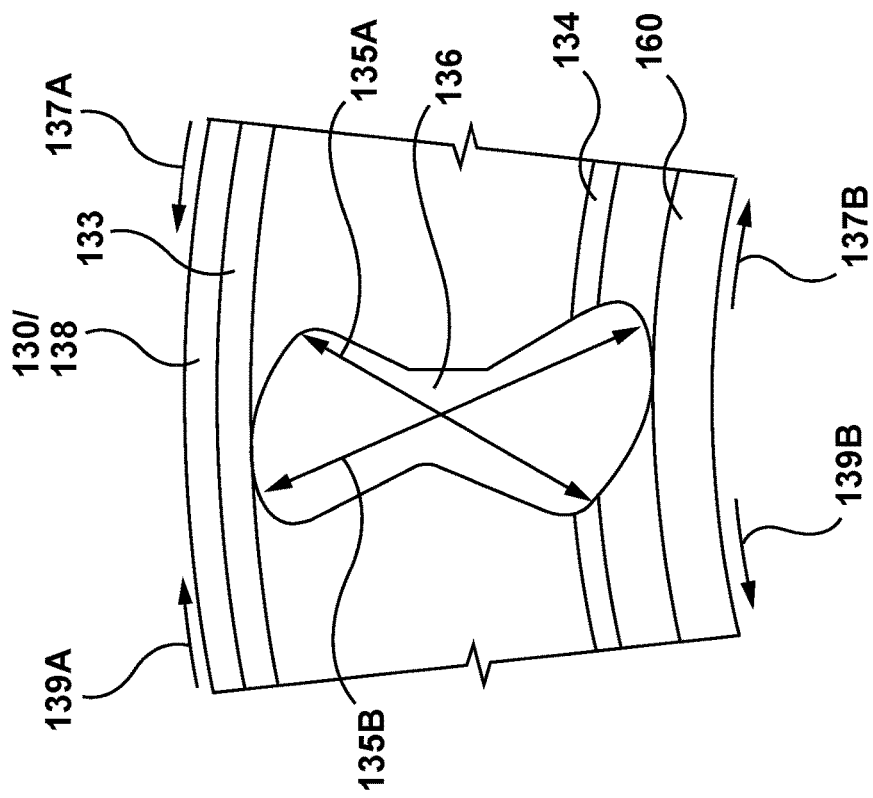
FIG. 10A is an enlarged view of a portion of the first one-way clutch of FIG. 10.
Figure 10:
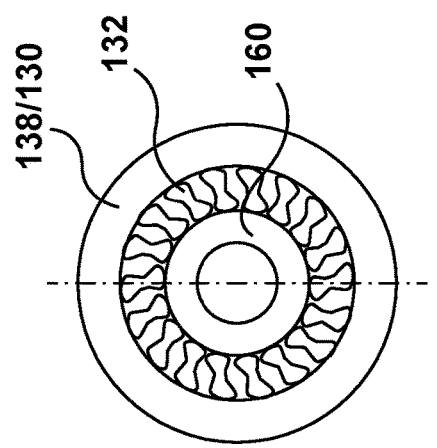
FIG. 10 is a sectional view of a first one-way clutch of the sheath retraction mechanism of FIG. 9.

More particularly, FIG. 10 is a sectional view of first one-way clutch 132 of sheath retraction mechanism 105 and FIG. 10A is an enlarged view of a portion of first one-way clutch 132. First pulley 130 is attached to first rotatable knob 138 so as to be rotatable therewith. First one-way clutch 132 is press fit into first pulley 130, thereby coupling the outer surface of one-way clutch 132 to first pulley 130 such that an outer portion or component of one-way clutch 132 rotates or turns with first pulley 130 as will be described in more detail herein. Joining shaft 160 is coupled to the inner surface of one-way clutch 132 via an interference or friction fit such that an inner portion or component of one-way clutch 132 rotates or turns with joining shaft 160 as will be described in more detail herein. First one-way clutch 132 does not transmit a torque from first pulley 130 to joining shaft 160 when first rotatable knob 138 is rotated in a first direction. In the embodiment of first one-way clutch 132 depicted in FIGS. 10-10A, the first direction is counter-clockwise. As a result, when first rotatable knob 138 is rotated in the first or counter-clockwise direction, first pulley 130 also rotates to wind up a portion of cable 140. However, since first one-way clutch 132 does not transmit a torque from first pulley 130 to joining shaft 160 when first rotatable knob 138 is rotated counter-clockwise, joining shaft 160 and second rotatable knob 158 do not rotate when first rotatable knob 138 is rotated in the first direction (i.e., counter-clockwise). First rotatable knob 138 thus operates independently of second rotatable knob 158 (i.e., can be turned on its own) such that second rotatable knob 158 remains stationary when first rotatable knob 138 is rotated in the first direction (i.e., counter-clockwise).

First one-way clutch 132 is a uni-directional or single direction clutch bearing that is designed to transmit torque or a drive between a first component and a second component in one direction and allow free motion or freewheel in the opposite direction. As utilized herein, first one-way clutch 132 is designed to transmit torque between first pulley 130/first rotatable knob 138 and joining shaft 160 in one direction and allow free motion or freewheel in the opposite direction. In an embodiment, as shown in FIGS. 10 and 10A, one-way clutch 132 may be a sprag clutch and include an annular outer support or component 133, an annular inner support or component 134, and a plurality of spring-loaded sprags 136 disposed between outer and inner supports 133, 134. The inner ends or surfaces of sprags 136 extend beyond inner support 134 and contact joining shaft 160 via an interference or friction fit therewith. When disposed within delivery system 100, outer support 133 of first one-way clutch 132 is coupled or attached to first pulley 130 of first rotatable knob 138 via a press fit and thereby may be considered to move concurrently as an ensemble or subassembly therewith. Sprag clutches are commercially available from Outrage RC, LLC of Malden, Mass., as well as various other manufacturers. Sprags 136 are configured to become wedged or locked between outer and inner supports 133, 134 when one of first pulley 130 or joining shaft 160 is rotated in a particular direction, and thereby transmit or convey torque from the rotated support member to the other support member. First one-way clutch 132 is configured to not transmit a torque from first pulley 130 to joining shaft 160 when first pulley 130 is rotated counter-clockwise. Stated another way, with respect to rotation of first pulley 130, first one-way clutch 132 freewheels or idles around joining shaft 160 in the counter-clockwise direction.

More particularly, sprags 136 of first one-way clutch 132 are configured to become wedged or locked between first pulley 130 and joining shaft 160 when first pulley 130 is rotated clockwise as indicated by directional arrow 139A and/or joining shaft 160 is rotated counter-clockwise as indicated by directional arrow 139B. As first pulley 130 rotates clockwise, sprags 136 pivot around their centerpoint and a larger height or dimension 135B of sprags 1150 wedges sprags 136 between first pulley 130 and joining shaft 160, thereby locking or engaging the components together. The same result occurs if joining shaft 160 is rotated counter-clockwise, i.e., first pulley 130 and joining shaft 160 engage or lock together if joining shaft 160 is rotated counter-clockwise. When first pulley 130 rotates counter-clockwise as indicated by directional arrow 137A, sprags 136 pivot around their centerpoint and a smaller height or dimension 135A of sprags 136 allows first pulley 130 to spin or rotate freely over or freewheel relative to joining shaft 160. The same result occurs if joining shaft 160 is rotated clockwise as indicated by directional arrow 137B, i.e., joining shaft 160 spins or rotates freely within first pulley 130 when joining shaft 160 is rotated in a clockwise direction. Rotation of first rotatable knob 138 in the first direction (i.e., counter-clockwise) causes first pulley 130 to rotate and first one-way clutch 132 freely spins within or over joining shaft 160 thereby causing first pulley 130 to wind up a portion of cable 140 and retract outer sheath 104 at a first speed. As such, first pulley 130 is configured to be rotated independently with rotation of first rotatable knob 138.

Figure 11A:
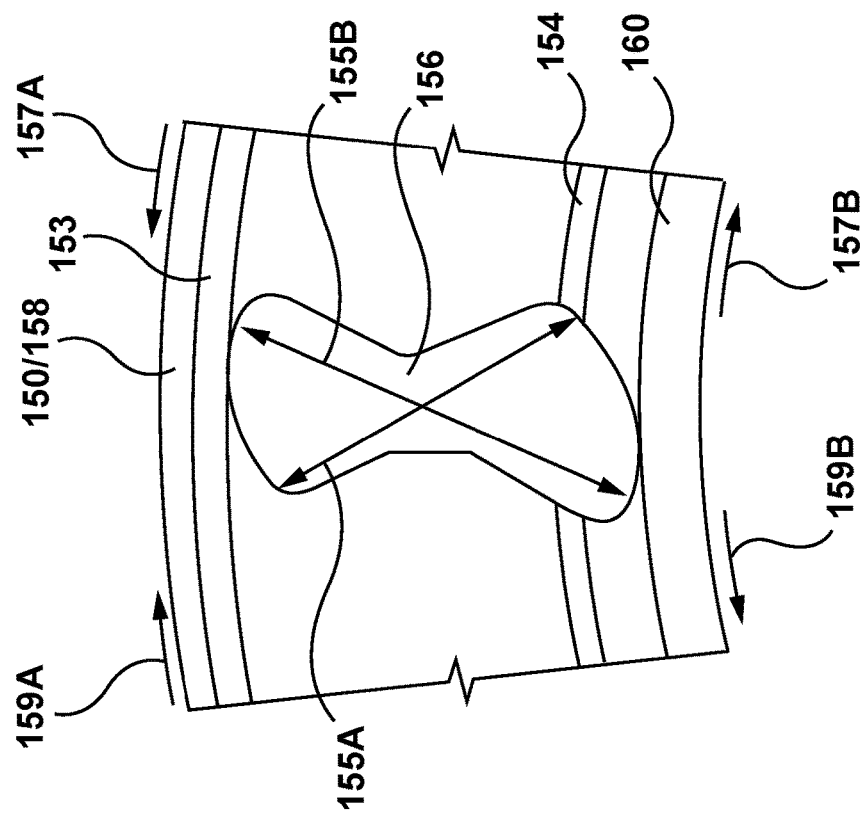
FIG. 11A is an enlarged view of a portion of the second one-way clutch of FIG. 11.
Figure 11:
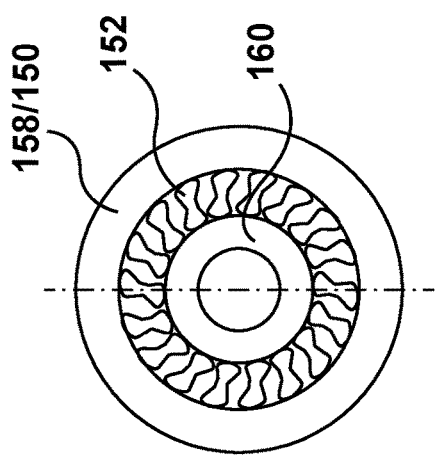
FIG. 11 is a sectional view of a second one-way clutch of the sheath retraction mechanism of FIG. 9.

Second one-way clutch 152 has an opposing or opposite configuration or orientation than first one-way clutch 138, meaning that second one-way clutch 152 is configured to transmit a torque from second pulley 150 to joining shaft 160 when second pulley 150 is rotated counter-clockwise. More particularly, the opposing orientations or configurations of clutches 132, 152 may be seen through a comparison of FIGS. 10-10A and 11-11A. FIG. 11 is a sectional view of second one-way clutch 152 of sheath retraction mechanism 105 and FIG. 11A is an enlarged view of a portion of second one-way clutch 152. Second one-way clutch 152 may also be a sprag clutch and include an annular outer support or component 153, an annular inner support or component 154, and a plurality of spring-loaded sprags 156 disposed between outer and inner supports 153, 154. The inner ends or surfaces of sprags 156 extend beyond inner support 154 and contact joining shaft 160 via an interference or friction fit therewith. When disposed within delivery system 100, outer support 153 of second one-way clutch 152 is coupled or attached to second pulley 150 of second rotatable knob 158 via a press fit and thereby may be considered to move concurrently as an ensemble or subassembly therewith.

In the configuration of FIGS. 11-11A, sprags 156 are configured to become wedged or locked between outer and inner supports 153, 154 when second pulley 150 is rotated in a counter-clockwise direction indicated by directional arrow 157A and/or when joining shaft 160 is rotated in a clockwise direction indicated by directional arrow 157B. As second pulley 150 rotates counter-clockwise, sprags 156 pivot around their centerpoint and a larger height or dimension 155B of sprag 156 wedges sprag 156 between outer and inner supports 153, 154, thereby locking or engaging the supports together so that they turn or rotate as one. Stated another way, second pulley 150 transmits or conveys torque to the joining shaft 160 when second pulley 150 is rotated counter-clockwise because the wedging action provides or transfers a drive from second pulley 150 to joining shaft 160. The same result occurs if joining shaft 160 is rotated in a second opposing direction or clockwise, i.e., outer and inner supports 153, 154 engage or lock together if joining shaft 160 is rotated clockwise. Conversely, when second pulley 150 rotates in a second opposing direction or clockwise as indicated by directional arrow 159A, sprags 156 pivot around their centerpoint and a smaller height or dimension 155A of sprag 156 disengages outer and inner supports 153, 154 and allows second pulley 150 and outer support 153 coupled thereto to spin over or freewheel relative to joining shaft 160. Stated another way, since sprags 156 are not wedged or locked between outer and inner supports 153, 154, second pulley 150 does not transmit or convey torque to the inner support when second pulley 150 is rotated in a clockwise direction. The same result occurs if joining shaft 160 is rotated counter-clockwise as indicated by directional arrow 159B, i.e., joining shaft 160 spins or rotates freely within second pulley 150 and outer support 153 coupled thereto when joining shaft 160 is rotated counter-clockwise. Stated another way, second one-way clutch 152 drives or rotates joining shaft 160 in the counter-clockwise direction and freewheels or idles around joining shaft 160 in the clockwise direction.

During operation, i.e., when second rotational knob 158 is rotated counter-clockwise, second pulley 150 rotates therewith and winds up a portion of cable 140. In addition, when second rotational knob 158 is rotated counter-clockwise, torque is transmitted to joining shaft 160 via second one-way clutch 152. When joining shaft 160 rotates counter-clockwise, i.e., as shown by the directional arrow 139B of FIG. 10A, first pulley 130 and joining shaft 160 engage or lock together via sprags 136 and thus first one-way clutch 132 drives first pulley 130 counter-clockwise such that first pulley 130 winds up a portion of cable 140. Stated another way, when second rotational knob 158 is rotated counter-clockwise, joining shaft 160 is driven counter-clockwise and first one-way clutch 132 transmits the counter-clockwise torque from joining shaft 160 to first pulley 130 to wind up cable 140. During this torque transmittal step, sprags 136 are wedged between joining shaft 160 and first pulley 130 so that sprags 136 transfers the counter-clockwise torque from joining shaft 160 to first pulley 130. As such, when second rotational knob 158 is rotated counter-clockwise, both first and second pulleys 130, 150 are concurrently rotated counter-clockwise to wind up a portion of cable 140. Rotation of second rotatable knob 158 in the first direction (i.e., counter-clockwise) causes both first and second pulleys 130, 150 to rotate via second one-way clutch 152 transmitting a torque from second pulley 150 to joining shaft 160 the joining shaft 160 transmitting a torque from second pulley 150 to first one-way clutch 132. First one-way clutch 132 then transmits a torque from joining shaft 160 to first pulley 130, thereby causing both first and second pulleys 130, 150 to wind up a portion of cable 140 and retract outer sheath 104 at a second speed that is faster than the first speed. Thus, when second rotational knob 158 is rotated counter-clockwise, second rotatable knob 158, second pulley 150, second one-way clutch 152, joining shaft 160, first one-way clutch 132, and first rotatable knob 138 all simultaneously rotate counter-clockwise as an ensemble.

During operation/rotation of first rotatable knob 138, tension may develop as first pulley 130 reels in cable 140 that retracts outer shaft 104. When first rotatable knob 138 is released, cable 140 in some instances may tend to slightly recoil and undesirably cause first pulley 130 to rotate in a second opposing direction (i.e., clockwise), thereby unreeling or unwinding cable 140 from first pulley 130. Thus, it is desirable to prevent undesired unwinding of cable 140 when first rotatable knob 138 is released. When first pulley 130 tries to unwind and rotate clockwise due to recoil of cable 140, such rotation of first pulley 130 is prevented due to first and second one-way clutches 132, 152. More particularly, when first pulley 130 tries to unwind and rotate clockwise, first one-way clutch 132 engages joining shaft 160 to rotate in the clockwise direction as well. However, joining shaft 160 does not rotate since rotation of joining shaft 160 in the clockwise direction also engages second one-way clutch 152 as well as second pulley 150 and second rotatable knob 158 coupled thereto. The unwinding or unreeling of cable 140 prevented because the force associated with the unwinding or unreeling is less than the force associated with rotation of an ensemble including first one-way clutch 132, joining shaft 160, second one-way clutch 152, second pulley 150, and second rotatable knob 158. Stated another way, since the disposition of cable 140 is balanced between first and second pulleys 130, 150, the tendency for cable 140 to unwind or unreel from only one of the pulleys (i.e., first pulley 130) is reduced or eliminated.

Although described as sprag-type clutches, in another embodiment hereof (not shown), first and/or second one-way clutches 132, 152 may be a roller-type clutch in which torque is positively transmitted by rollers that wedge against interior ramps or may be another type of uni-directional clutch known in the art. Further, although the first direction is counter-clockwise in the embodiment of first one-way clutch 132 depicted in FIGS. 10-10A, it will be understood by one of ordinary skill in the art that first one-way clutch 132 may have an opposite configuration such that the first direction is clockwise as long as first one-way clutch 132 and second one-way clutch 152 have opposite configurations.

With first and second one-way clutches 132, 152 described in detail, the operation or method of use of sheath retraction mechanism 105 will now be described with reference to FIG. 9. When it is desired to deploy prosthesis 101, first rotatable knob 138 is turned or rotated in a counter-clockwise direction. As described above, counter-clockwise rotation of first rotatable knob 138 causes first pulley 130 to rotate thereby causing first pulley 130 to wind up a portion of cable 140 and retract outer sheath 104 at a first speed. At this stage in the method of use, first one-way clutch 132 freely spins within or over joining shaft 160. First rotatable knob 138 is turned or rotated until distal end 108 of outer sheath 104 no longer covers or extends over the proximal end of prosthesis 101, at which point flag 128 pops up to indicate that this position of outer sheath 104. As described above with respect to FIG. 3, the first step or stage of tip release is now performed by rotating grip component 123 in the first direction until distal sleeve 121 of tip capture device 125 has been distally advanced a sufficient distance to partially uncover the proximal end of prosthesis 101, which permits prosthesis 101 to transition from a delivery state to a partially deployed state. With the proximal end of prosthesis 101 in the partially deployed state, a clinician via fluoroscopy may assure proper positioning at a treatment site of the proximal end of prosthesis 101 before full deployment of prosthesis 101. Accordingly, if the proximal end of prosthesis 101 is found to be not properly positioned at this stage of the procedure, the clinician may "push" or otherwise manipulate the proximal end of prosthesis 101 until proper placement is confirmed.

After all desired adjustments have been made to the position of prosthesis 101, second rotatable knob 158 is turned or rotated in a counter-clockwise direction. As described above, counter-clockwise rotation of second rotatable knob 158 causes both first and second pulleys 130, 150 to concurrently rotate counter-clockwise to wind up a portion of cable 140 via second one-way clutch 152. Second one-way clutch 152 drives joining shaft 160 in a counter-clockwise direction, which in turn drives first one-way clutch 132 and first pulley 130 coupled thereto in a counter-clockwise direction. When both first and second pulleys 130, 150 rotate to wind up a portion of cable 140, outer sheath 104 is retracted at a second speed that is faster than the first speed. Second rotatable knob 158 is turned or rotated until outer sheath 104 no longer covers or extends over prosthesis 101 and the length of prosthesis 101 is completely uncovered. Each time second rotatable knob 158 is turned or rotated, a portion of the length of cable 140 is wound each of first and second pulleys 130, 150. As cable 140 is wound or circled around first and second pulleys 130, 150, outer sheath 104 moves proximally and axially with respect to housing 103 of housing 102. Repeated turning of second rotatable knob 158 results in continued winding of cable 140 and outer sheath 104 is incrementally withdrawn to release prosthesis 101. In an embodiment hereof, three rotations or revolutions of second rotatable knob 158 proximally retracts or withdraws outer sheath 104 to fully deploy or release prosthesis 101. However, as will be understood by one of ordinary skill in the art, the time required for full retraction of outer sheath 104 may vary depending upon the length of prosthesis 101, the distance that outer sheath 104 is required to travel in order to fully release the prosthesis, whether the user selects to use one or two pulleys and how much of cable 140 is wound per rotation of the pulleys. As also will be understood by one of ordinary skill in the art, the length of cable 140 wound with each rotation of the pulleys may be varied by changing the size of first and second pulleys 130, 150. For example, in an embodiment, the size/diameter of at least second pulley 150 may be increased in order to increase the rate at which outer sheath 104 is proximally retracted when both first and second pulleys 130, 150 are rotating.

At this point of operation, prosthesis 101 is no longer covered by outer sheath 104 but the proximal end of prosthesis 101 is still coupled to tip capture device 125. Thus, as described above with respect to FIG. 3, the second step or stage of tip release is now performed by rotating grip component 123 in the second direction until distal sleeve 121 of tip capture device 125 is distal of the proximal end of prosthesis 101 such that the proximal end of prosthesis 101 releases from or moves free of tip capture device 125 and the proximal end of prosthesis 101 transitions from the partially deployed state to a fully deployed state. With the release of the proximal end of prosthesis 101 from tip capture device 125, prosthesis 101 is fully deployed. In another embodiment, the second step or stage of tip release can occur immediately after the first step or stage of tip release (i.e., after the necessary adjustments to the position of prosthesis 101 are made) but prior to fully retracting outer sheath 104 via second rotatable knob 158. Rather, second rotatable knob 158 is rotated to fully retract outer sheath 104 at the second, faster speed after the second step or stage of tip release is performed by rotating grip component 123 in the second direction until distal sleeve 121 of tip capture device 125 is distal of the proximal end of prosthesis 101.

FIGS. 12-19 illustrate a delivery system 1200 having a handle 1202 according to another embodiment hereof. Similar to delivery system 100, delivery system 1200 is configured such that a user may select whether to retract an outer sheath 1204 thereof with one pulley at a first speed or to retract outer sheath 1204 with two pulleys at a second speed, which is faster than the first speed. However, in delivery system 1200, first and second rotatable knobs 1238, 1258 are disposed on the same side of handle 1202 and are collinear. During use, delivery systems are often laid down on a patient's leg. As such, positioning both knobs 1238, 1258 on the same side of delivery system 1200 allows a physician to place delivery system 1200 flat on the patient's leg with both knobs 1238, 1258 pointing upward for ease of use.

Figure 14:
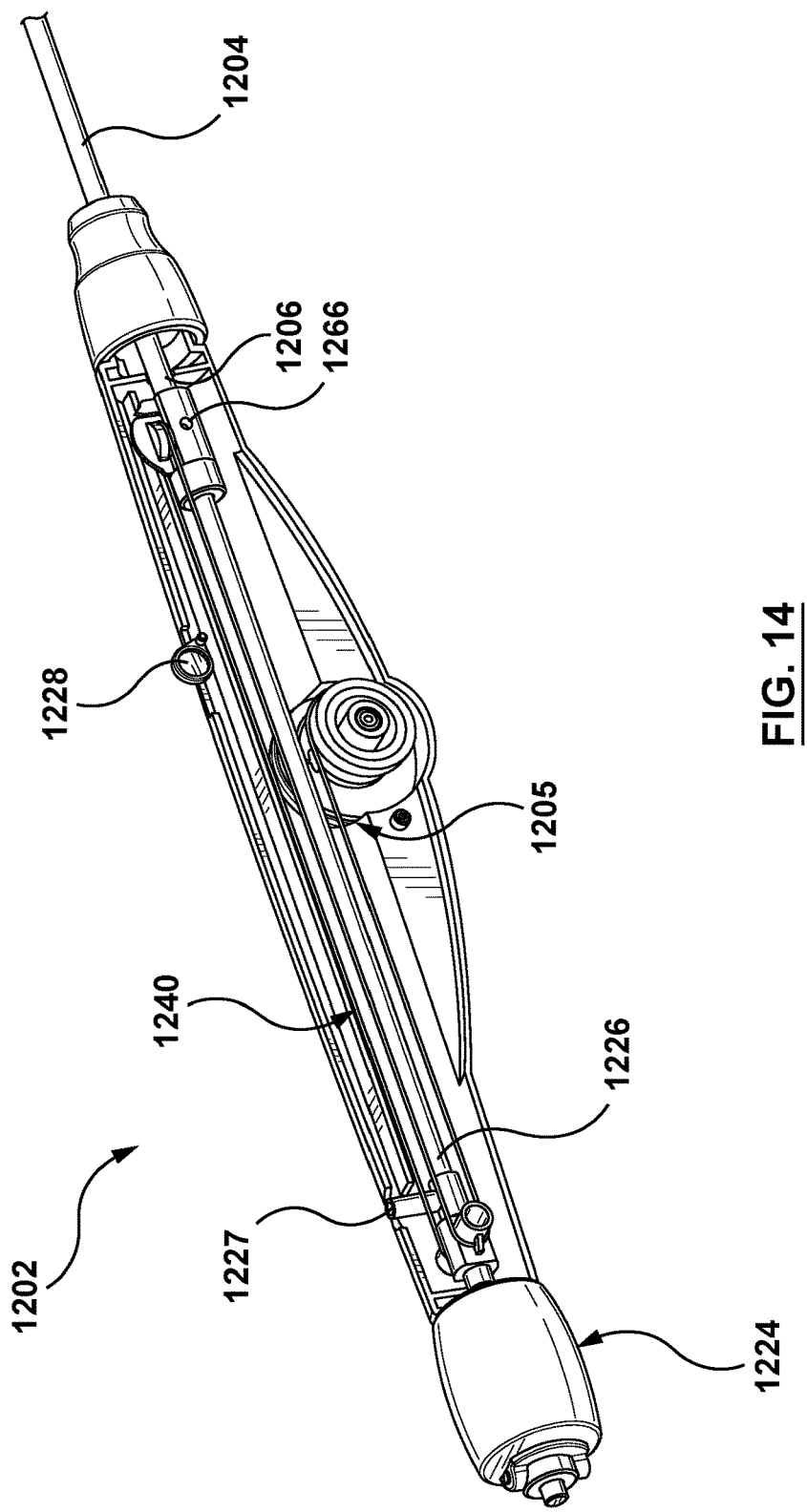
FIG. 14 is a perspective view of the handle of the delivery system of FIG. 12, wherein a portion of a housing of the handle has been removed for illustrative purposes.

FIGS. 12-13 are perspective and top views, respectively, of handle 1202 of delivery system 1200, and FIG. 14 is a perspective view of handle 1202 with a portion of a housing 1303 of handle 1202 removed to illustrate the internal components of handle 1202. Similar to delivery system 100, delivery system 1200 also includes an inner shaft 1212 and both outer sheath 1204 and inner shaft 1212 extend from within housing 1303 of handle 1202. Outer sheath 1204 and inner shaft 1212 are the same as outer sheath 104 and inner shaft 112, respectively, described above. Handle 1202 includes tip capture mechanism 1224, which is the same as tip capture mechanism 124 as described above with respect to FIG. 3. Handle 102 also includes a flush shaft or lumen 1226 having a port 1227 which are similar to flush shaft 126 and port 127 described above. Similarly, handle 102 includes a flag 1228 which is the same as flag 128 described above. Handle 1202 further includes a sheath retraction mechanism 1205 for retracting outer sheath 1204 as will be explained in more detail herein with respect to FIGS. 15-19. A proximal end 1206 of outer sheath 1204 is operably coupled to sheath retraction mechanism 1305 of handle 1202 and during deployment of prosthesis 101, sheath retraction mechanism 1305 is operated via an first and second rotatable knobs 1238, 1258 in order to proximally retract outer sheath 1204 to thereby incrementally expose prosthesis 101 and, once prosthesis 101 is properly positioned, to permit the full release of prosthesis 101 from delivery system 1200, as explained in more detail below.

Sheath retraction mechanism 1205 for retracting outer sheath 1204 will now be described in more detail with respect to FIGS. 15-19. Similar to sheath retraction mechanism 105, sheath retraction mechanism 1205 includes first rotatable knob 1238 accessible from an exterior of housing 1203 of handle 1202, a first pulley 1230 coupled to first rotatable knob 1238 so as to be rotatable therewith, a second rotatable knob 1258 accessible from an exterior of housing 103 of handle 1202, a second pulley 1250 coupled to second rotatable knob 1258 so as to be rotatable therewith, and a single continuous cable 1240. Each of first and second pulleys 1230, 1250 include a circumferential groove or channel formed on an outer surface thereof for receiving single continuous cable 1240. As will be explained in more detail herein, rotation of first rotatable knob 1238 in the first direction (i.e., counter-clockwise) causes first pulley 1230 to rotate while second pulley 1250 remains stationary thereby causing first pulley 1230 to wind up a portion of cable 1240 and retract outer sheath 1204 at a first speed. Rotation of second rotatable knob 1250 in the first direction (i.e., counter-clockwise) causes both first and second pulleys 1230, 1250 to rotate, thereby causing both first and second pulleys 1230, 1250 to wind up a portion of cable 1240 and retract outer sheath 1204 at a second speed that is faster than the first speed since both pulleys are rotating.

Figure 15:
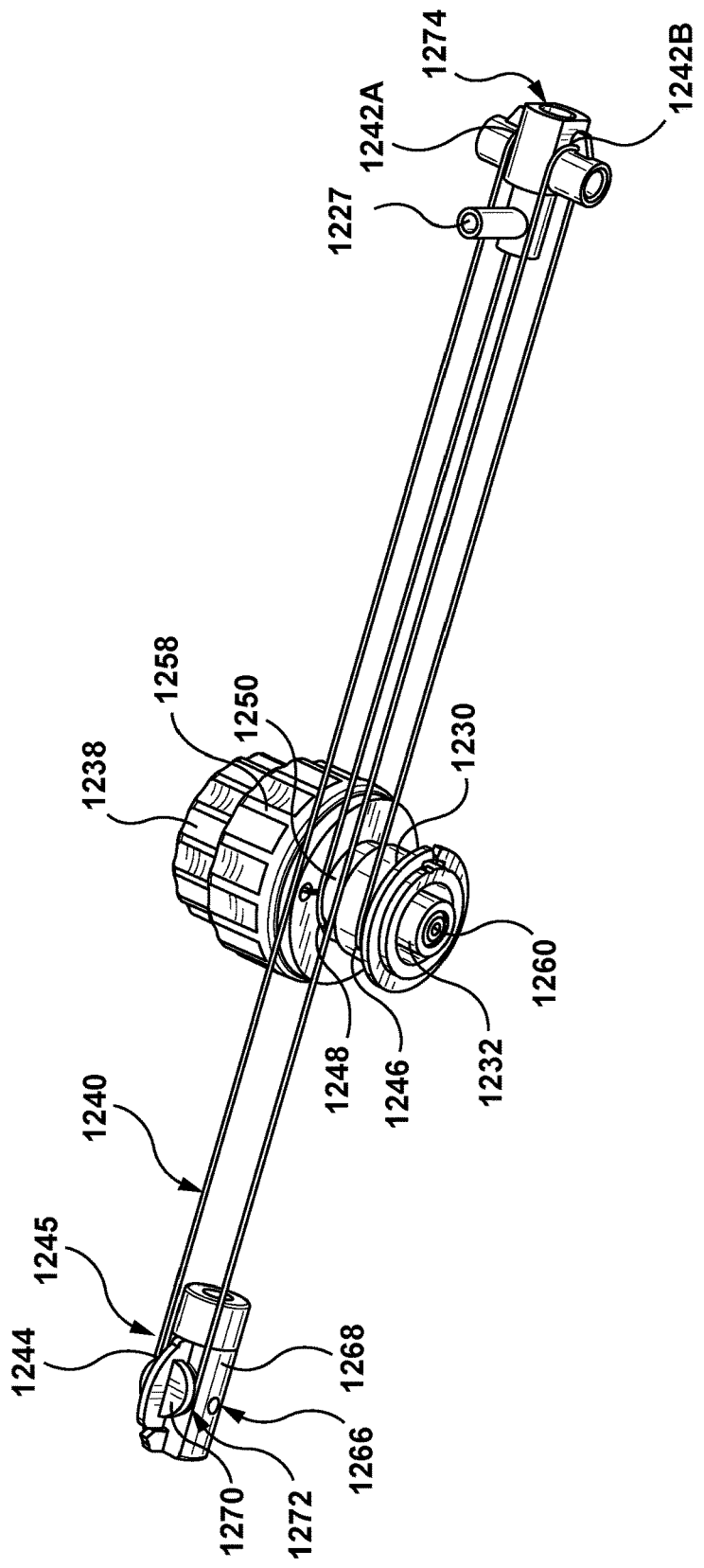
FIG. 15 is a perspective view of select components of the handle of the delivery system of FIG. 12 to illustrate a single continuous cable of the handle of the delivery system of FIG. 12, wherein the other components of the handle have been removed for illustrative purposes.

FIG. 15 is a perspective view of select components of handle 1202 to illustrate operation of first and second pulleys 1230, 1250 with single continuous cable 1240. Housing 1203 and various other components of the handle have been removed to isolate components described in relation to FIG. 15. In addition to first and second pulleys 1230, 1250, sheath retraction mechanism 1205 further includes single continuous cable 1240 having a first end 1246 coupled to first pulley 1230, a second end 1248 coupled to second pulley 1250, and an intermediate portion 1245 coupled to proximal end 1206 of outer sheath 1204. Single continuous cable 1240 may be formed from any sufficiently strong suitable material, including but not limited to Kevlar® or other suitable synthetic fiber. Intermediate portion 1245 of single continuous cable 1240 is coupled to proximal end 1206 of outer sheath 1204 via anchor 1266. Anchor 1266 includes an annular portion 1268 which surrounds and attaches to or is mounted over proximal end 1206 of outer sheath 1204. Anchor 166 further includes a stem or tab 1270 that extends from annular portion 168 and includes a circumferential channel or track 1272 formed thereon. Intermediate portion 1245 of single continuous cable 1240 includes a distal loop 1244 that extends around circumferential channel or track 1272 of anchor 1266 in order to couple the intermediate portion of the single continuous cable to proximal end 1206 of outer sheath 1204. Notably, single continuous cable 1240 also includes a second intermediate portion having two proximal loops 1242A, 1242B that each extend around a portion of a mount 1274 that includes port 1227 for flush lumen 1226. Proximal loops 1242A, 1242B each extend around an outer surface of mount 1274. As such, single continuous cable 1240 is an elongated element with first end 1246 coupled to first pulley 1230, second end 1248 coupled to second pulley 1250, and the length of single continuous cable 1240 is looped around anchor 1266 and mount 1274. Utilizing a single continuous cable that winds around both first and second pulleys 1230, 1250 rather than two separate cables provides a mechanical advantage that amplifies the force applied for retracting outer sheath 1204 as described above with respect to single continuous cable 140.

Figure 17:
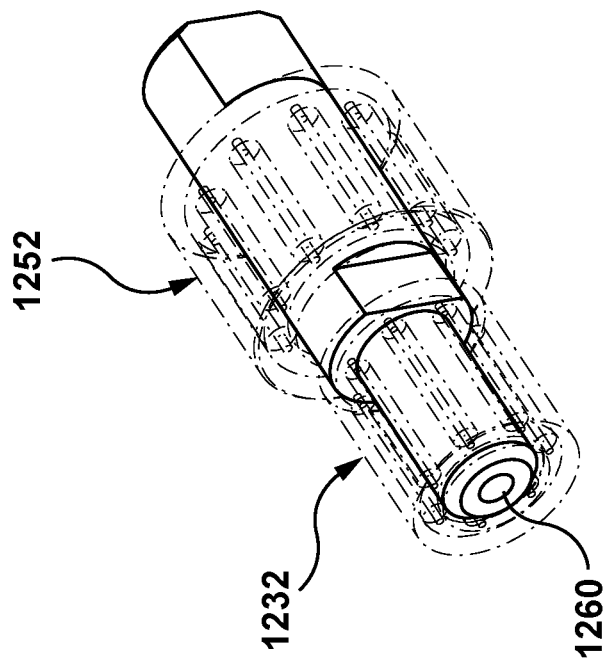
FIG. 17 is a perspective view of a first and second one-way clutches disposed over a joining shaft to illustrate select components of the sheath retraction mechanism of the handle of the delivery system of FIG. 12, wherein the first and second one-way clutches are shown in phantom for illustrative purposes.
Figure 16:
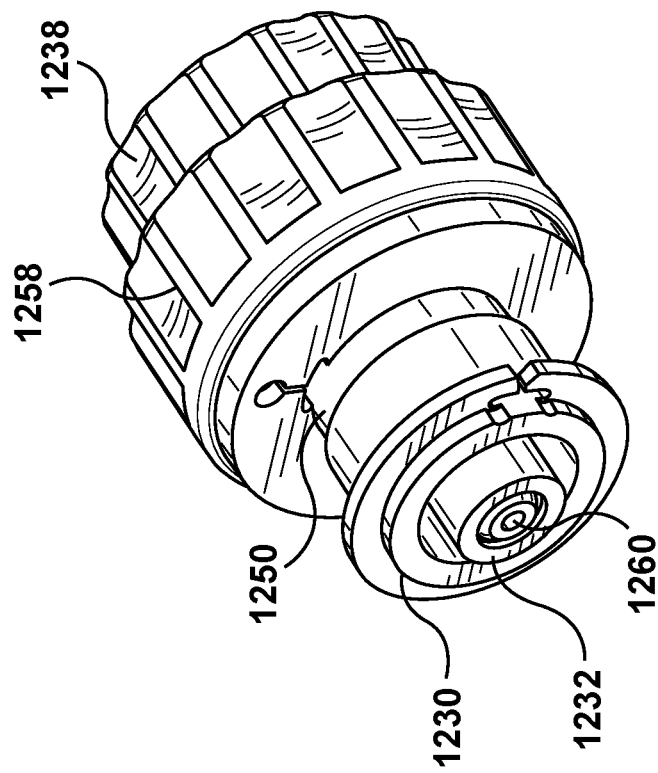
FIG. 16 is a perspective view of components of a sheath retraction mechanism of the handle of the delivery system of FIG. 12, wherein the other components of the handle have been removed for illustrative purposes.

The components and operation of sheath retraction mechanism 1205 will now be described in more detail with reference to FIGS. 16-19. FIG. 16 is a perspective view of select components of sheath retraction mechanism 1205. In particular, FIG. 16 illustrates a joining shaft 1260, a first one-way clutch 1232 disposed over joining shaft 1260 and coupled to first pulley 1230 and first rotatable knob 1238, and a second one-way clutch 1252 (shown in FIG. 17) disposed over joining shaft 1260 and coupled to second pulley 1250 and second rotatable knob 1258. FIG. 17 illustrates joining shaft 1260 with first and second one-way clutches 1232, 1252 disposed thereover in phantom.

Figure 18:
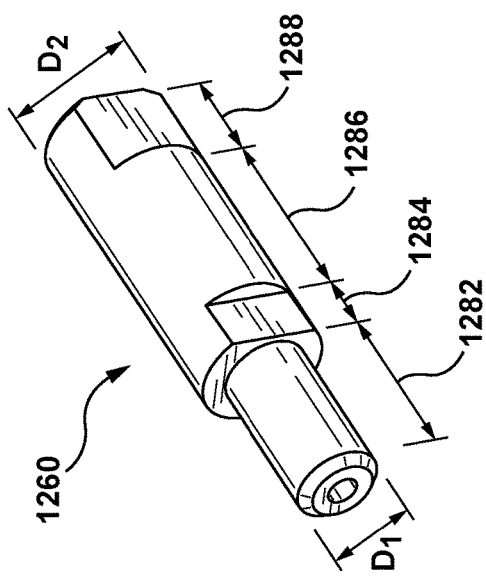
FIG. 18 is a perspective view of the joining shaft of FIG. 17.
Figure 20:
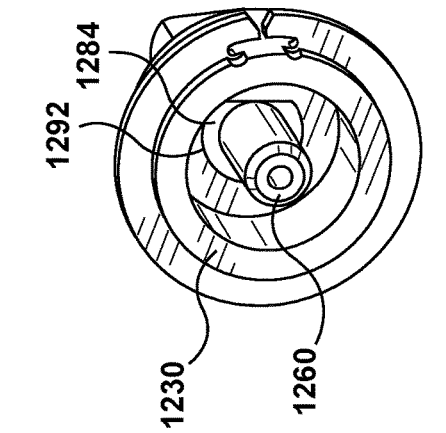
FIG. 20 is a perspective view of select components of the sheath retraction mechanism of the handle of the delivery system of FIG. 12 to illustrate the coupling between the joining shaft and a first pulley of the sheath retraction mechanism.
Figure 19:
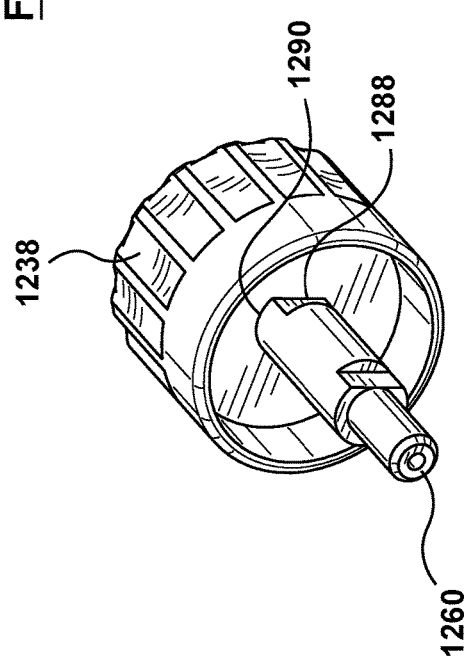
FIG. 19 is a perspective view of select components of the sheath retraction mechanism of the handle of the delivery system of FIG. 12 to illustrate the coupling between the joining shaft and a first rotatable knob of the sheath retraction mechanism.

FIGS. 18-20 illustrate how first pulley 1230 is coupled to first rotatable knob 1238 so as to be rotatable therewith. FIG. 18 illustrates a perspective view of joining shaft 1260 removed from delivery system 1200 for illustrative purposes. Joining shaft 1260 includes four longitudinal portions or sections (first longitudinal portion 182, second longitudinal portion 184, third longitudinal portion 186, and fourth longitudinal portion 188) that collectively form joining shaft 1260. First and third longitudinal portions 182, 186 each have a circular cross-section, with first longitudinal portion 182 having a diameter Di that is smaller than diameter D2 of third longitudinal portion 186. Second and fourth longitudinal portions 184, 188 each have a non-circular cross-section. In an embodiment, the non-circular cross-section of second and fourth longitudinal portions 184, 188 of joining shaft 1260 may be generally D-shaped. The D-shaped cross-section of second and fourth longitudinal portions 184, 188 may be formed by removing or cutting away a portion of joining shaft 1260, although other manufacturing processes may also be used. As best shown in FIG. 19, which is an end view of joining shaft 1260 within first rotatable knob 1238, first rotatable knob 1238 has an inner surface 1290 which mates with the outer surface of fourth longitudinal portion 1288 of joining shaft 1260. Joining shaft 1260 is effectively coupled to first rotatable knob 1238 by the mating non-circular surfaces between fourth longitudinal portion 1288 of joining shaft 1260 and inner surface 1290 of first rotatable knob 1238. Accordingly, joining shaft 1260 turns or spins in the same direction as and with first rotatable knob 1238 as one. Similarly, as best shown in FIG. 20 which is an end view of joining shaft 1260 within first pulley 1230, first pulley 1230 has an inner surface 1292 which mates with the outer surface of second longitudinal portion 184 of joining shaft 1260. Joining shaft 1260 is effectively coupled to first pulley 1230 by the mating non-circular surfaces between second longitudinal portion 184 of joining shaft 1260 and inner surface 1292 of first pulley 1230. Accordingly, first pulley 1230 turns or spins in the same direction as and with joining shaft 1260 as one. Thus, the mating non-circular surfaces between first rotatable knob 1238 and joining shaft 1260 and the mating non-circular surfaces between joining shaft 160 and first pulley 1230 effectively couple first rotatable knob 1238 and first pulley 1230 together such that these components turn or spin together as an ensemble.

Figure 21:
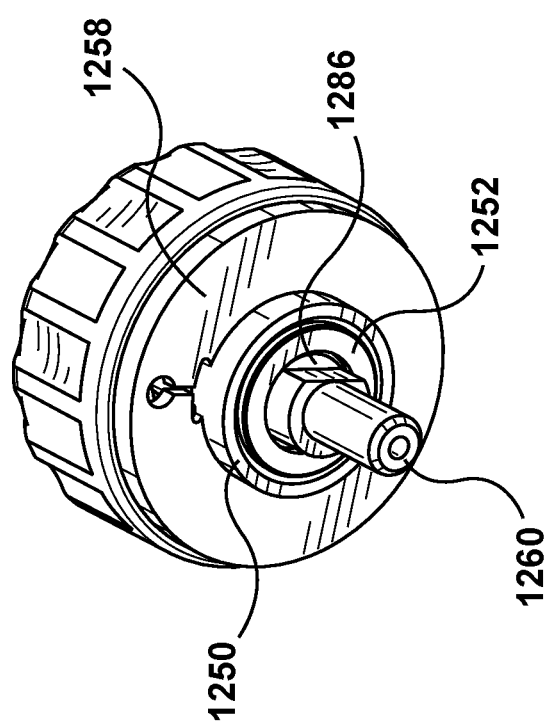
FIG. 21 is a perspective view of select components of the sheath retraction mechanism of the handle of the delivery system of FIG. 12 to illustrate the coupling between a second rotatable knob, a second pulley, and the joining shaft of the sheath retraction mechanism.

With reference to FIG. 21, second pulley 1250 is attached to second rotatable knob 1258 so as to be rotatable therewith. Further, second one-way clutch 1252 is press fit into second pulley 1250, thereby coupling the outer surface of second one-way clutch 1252 to second pulley 1250 such that an outer portion or component of second one-way clutch 1252 rotates or turns with second pulley 1250 as described above with respect to second one-way clutch 152.

As best shown in FIG. 17, first one-way clutch 1232 is disposed over first longitudinal portion 1282 of joining shaft 1260 and joining shaft 1260 is coupled to the inner surface of first one-way clutch 1232 via an interference or friction fit such that an inner portion or component of first one-way clutch 1232 rotates or turns with joining shaft 1260 as described above with respect to first one-way clutch 132 (i.e., first one-way clutch 1232 rotates or turns with joining shaft 1260 when joining shaft 1260 rotates in the counter-clockwise direction). Similarly, as shown in FIG. 17 and FIG. 21, second one-way clutch 1252 is disposed over third longitudinal portion 1286 of joining shaft 1260 and joining shaft 1260 is coupled to the inner surface of second one-way clutch 1252 via an interference or friction fit such that an inner portion or component of second one-way clutch 1252 rotates or turns with joining shaft 1260 as described above with respect to second one-way clutch 1252 (i.e., joining shaft 1260 rotates or turns with second one-way clutch 1252 when second one-way clutch 1252 rotates in the counter-clockwise direction).

First one-way clutch 1232 has a configuration similar to and operates similar to first one-way clutch 132 described above with respect to FIG. 10-10A, such that first one-way clutch 1232 does not transmit a torque from first pulley 1230 to joining shaft 1260 when first rotatable knob 1238 is rotated in the first direction, i.e., counter-clockwise. First rotatable knob 1238 thus operates independently of second rotatable knob 1258 (i.e., can be turned on its own) such that second rotatable knob 1258 remains stationary when first rotatable knob 138 is rotated in the first direction (i.e., counter-clockwise). Similarly, second one-way clutch 1252 has a configuration similar to and operates similar to second one-way clutch 152 described above with respect to FIG. 11-11A, such that second one-way clutch 1252 does transmit a torque from second pulley 1250 to joining shaft 1260 when second rotatable knob 1258 is rotated in the first direction, i.e., counter-clockwise. When second rotational knob 1258 is rotated counter-clockwise, both first and second pulleys 1230, 1250 are concurrently rotated counter-clockwise to wind up a portion of cable 1240 as described above with respect to second rotational knob 158. As such, first and second pulleys 1230, 1250 are configured to be rotated simultaneously with rotation of second rotatable knob 1258 to retract outer sheath 1204 at a second, faster rate than when only first pulley 1230 rotates.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery system for delivering a prosthesis, the delivery system comprising:
   a housing;
   a sheath extending from within the housing;
   a first rotatable knob accessible from an exterior of the housing;
   a first pulley coupled to the first rotatable knob so as to be rotatable therewith;
   a second rotatable knob accessible from an exterior of the housing;
   a second pulley coupled to the second rotatable knob so as to be rotatable therewith;
   at least one cable coupled to both the first pulley and the second pulley, wherein the at least one cable is coupled to a proximal portion of the sheath and rotation of the first rotatable knob causes the first pulley to rotate while the second pulley remains stationary thereby causing only the first pulley to wind up a portion of the at least one cable and retract the sheath at a, first speed, and rotation of the second rotatable knob causes both the first and second pulleys to rotate, thereby causing both the first and second pulleys to wind up a portion of the at least one cable and retract the sheath at a second speed, the second speed being faster than the first speed.

2. The delivery system of claim 1, wherein the at least one cable is a single continuous cable having a first end coupled to the first pulley and a second end coupled to the second pulley.

3. The delivery system of claim 2, wherein an anchor is attached to the proximal portion of the sheath and an intermediate portion of the single continuous cable is looped through a passageway formed in the anchor in order to couple the intermediate portion of the single continuous cable to the proximal portion of the sheath.

4. The delivery system of claim 3, wherein a second intermediate portion of the single continuous cable is looped around a portion of a mount housed within the handle.

5. The delivery system of claim 1, wherein the first and the second rotatable knobs are disposed on opposing sides of the handle.

6. The delivery system of claim 1, wherein the first nd second rotatable knobs are disposed on the same side of the handle and are collinear.

7. The delivery system of claim 1, further comprising:
a joining shaft;
a first one-way clutch disposed over the joining shaft and attached to the first pulley, wherein the first one-way clutch freely spins within or over the joining shaft when the first rotatable knob is rotated in a first direction; and
a second one-way clutch disposed over the joining shaft and attached to the second pulley, wherein the second one-way clutch transmits a torque from the second pulley to the joining shaft when the second rotatable knob is rotated in the first direction.

8. The delivery system of claim 7, wherein the joining shaft transmits a torque from the second pulley to the first one-way clutch and the first one-way clutch transmits a torque from the joining shaft to the first pulley when the second rotatable knob is rotated in the first direction.

9. The delivery system of claim 1, wherein the first and second pulleys are configured to be rotated simultaneously with rotation of the second rotatable knob.

10. The delivery system of claim 1, wherein the first pulley is configured to be rotated independently with rotation of the first rotatable knob.

11. A delivery system for delivering a prosthesis, the delivery system comprising:
a housing;
a sheath extending from within the housing;
a first rotatable knob accessible from an exterior of the housing;
a first pulley coupled to the first rotatable knob so as to be rotatable therewith;
a second rotatable knob accessible from an exterior of the housing;
a second pulley coupled to the second rotatable knob so as to be rotatable therewith, wherein the first pulley is configured to be rotated independently with rotation of the first rotatable knob and wherein the first and second pulleys are configured to be rotated simultaneously with rotation of the second rotatable knob;
at least one cable coupled to both the first pulley and the second pulley, wherein the at least one cable is coupled to a proximal portion of the sheath and rotation of the first rotatable knob causes only the first pulley to wind up a portion of the at least one cable and retract the sheath at a first speed, and rotation of the second rotatable knob causes both the first and second pulleys to wind up a portion of the at least one cable and retract the sheath at a second speed, the second speed being faster than the first speed.

12. The delivery system of claim 11, wherein the at least one cable is a single continuous cable having a first end coupled to the first pulley and a second end coupled to the second pulley.

13. The delivery system of claim 12, wherein an anchor is attached to the proximal portion of the sheath and an intermediate portion of the single continuous cable is looped through a passageway formed in the anchor in order to couple the intermediate portion of the single continuous cable to the proximal portion of the sheath.

14. The delivery system of claim 13, wherein a second intermediate portion of the single continuous cable is looped around a portion of a mount housed within the handle.

15. The delivery system of claim 11, wherein the first and the second rotatable knobs are disposed on opposing sides of the handle.

16. The delivery system of claim 11, wherein the first and second rotatable knobs are disposed on the same side of the handle and are collinear.

17. The delivery system of claim 11, further comprising:
a joining shaft;
a first one-way clutch disposed over the joining shaft and attached to the first pulley, wherein the first one-way clutch freely spins within or over the joining shaft when the first rotatable knob is rotated in a first direction; and
a second one-way clutch disposed over the joining shaft and attached to the second pulley, wherein the second one-way clutch transmits a torque from the second pulley to the joining shaft when the second rotatable knob is rotated in the first direction.

18. The delivery system of claim 17, wherein the joining shaft transmits a torque from the second pulley to the first one-way clutch and the first one-way clutch transmits a torque from the joining shaft to the first pulley when the second rotatable knob is rotated in the first direction.

19. A delivery system for delivering a prosthesis, the delivery system comprising:
a housing;
a sheath extending from within the housing;
a first rotatable knob accessible from an exterior of the housing;
a first pulley coupled to the first rotatable knob so as to be rotatable therewith;
a second rotatable knob accessible from an exterior of the housing;
a second pulley coupled to the second rotatable knob so as to be rotatable therewith;
a joining shaft;
a first one-way clutch disposed over the joining shaft and attached to the first pulley;
a second one-way clutch disposed over the joining shaft and attached to the second pulley; and
a single continuous cable having a first end coupled to the first pulley and a second end coupled to the second pulley, wherein the single continuous cable is coupled to a proximal portion of the sheath and rotation of the first rotatable knob causes the first pulley to rotate and the first one-way clutch freely spins within or over the joining shaft thereby causing the first pulley to wind up a portion of the at least one cable and retract the sheath at a first speed, and rotation of the second rotatable knob causes both the first and second pulleys to rotate via the second one-way clutch transmitting a torque from the second pulley to the joining shaft, thereby causing both the first and second pulleys to wind up a portion of the at least one cable and retract the sheath at a second speed, the second speed being faster than the first speed.

20. The delivery system of claim 19, further comprising:
a tip capture mechanism disposed at a proximalmost end of the handle.

* * * * *